(12) United States Patent
Dejima

(10) Patent No.: US 10,492,665 B2
(45) Date of Patent: *Dec. 3, 2019

(54) SURGICAL APPARATUS FOR ENDOSCOPE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 301 days.

This patent is subject to a terminal disclaimer.

(21) Appl. No.: 15/470,917

(22) Filed: Mar. 28, 2017

(65) Prior Publication Data

US 2017/0196440 A1    Jul. 13, 2017

Related U.S. Application Data

(63) Continuation of application No. PCT/JP2015/077585, filed on Sep. 29, 2015.

(Continued)

(51) Int. Cl.
*A61B 1/00* (2006.01)
*A61B 17/34* (2006.01)
(Continued)

(52) U.S. Cl.
CPC ........ *A61B 1/00135* (2013.01); *A61B 1/0052* (2013.01); *A61B 1/00128* (2013.01);
(Continued)

(58) Field of Classification Search
None
See application file for complete search history.

(56) References Cited

U.S. PATENT DOCUMENTS 4,748,969 A   6/1988  Wardle
5,373,840 A  12/1994  Knighton
(Continued)

FOREIGN PATENT DOCUMENTS

EP   2027811   2/2009
EP   2163217   3/2010
(Continued)

OTHER PUBLICATIONS

"International Preliminary Report on Patentability (Form PCT/IPEA/409) of PCT/JP2015/077585", with English translation thereof, Date of completion: Dec. 1, 2016, pp. 1-6.

(Continued)

*Primary Examiner* — Timothy J Neal
*Assistant Examiner* — Aaron B Fairchild
(74) *Attorney, Agent, or Firm* — JCIPRNET

(57) ABSTRACT

Provided is a surgical apparatus for an endoscope that can appropriately and easily perform mounting work of an endoscope onto an outer tube. An outer tube, which passes through a body wall, is inserted into a body cavity, and guides an endoscope and a treatment tool into the body cavity, includes a slider that is an interlocking member that moves the endoscope and the treatment tool forward and backward in an interlocking manner. At the time of mounting of an endoscope in which an endoscope insertion part is coupled to a slider body of the slider, the endoscope insertion part is inserted to a position where a larger-diameter part provided in the endoscope insertion part abuts against a base end surface of an outer tube. Accordingly, the slider body can be coupled to a predetermined suitable position of the endoscope insertion part.

8 Claims, 22 Drawing Sheets

Related U.S. Application Data

(60) Provisional application No. 62/057,525, filed on Sep. 30, 2014.

(51) Int. Cl.
*A61B 1/018* (2006.01)
*A61B 1/005* (2006.01)
*A61B 1/313* (2006.01)
*A61B 17/00* (2006.01)
*A61B 1/05* (2006.01)
*A61B 1/06* (2006.01)
*A61B 1/07* (2006.01)

(52) U.S. Cl.
CPC .......... *A61B 1/00154* (2013.01); *A61B 1/018* (2013.01); *A61B 17/34* (2013.01); *A61B 17/3415* (2013.01); *A61B 17/3421* (2013.01); *A61B 1/00133* (2013.01); *A61B 1/00188* (2013.01); *A61B 1/05* (2013.01); *A61B 1/0669* (2013.01); *A61B 1/07* (2013.01); *A61B 1/3132* (2013.01); *A61B 17/00234* (2013.01); *A61B 2017/00296* (2013.01); *A61B 2017/00438* (2013.01); *A61B 2017/3445* (2013.01)

(56) References Cited

U.S. PATENT DOCUMENTS

| | | | |
|---|---|---|---|
| 5,913,870 | A | 6/1999 | DeFonzo et al. |
| 2005/0070764 | A1 | 3/2005 | Nobis et al. |
| 2005/0119525 | A1 | 6/2005 | Takemoto |
| 2005/0228228 | A1 | 10/2005 | Boulais |
| 2008/0033238 | A1 | 2/2008 | Takahashi |
| 2008/0076966 | A1 | 3/2008 | Isaacson |
| 2015/0080650 | A1 | 3/2015 | Dejima et al. |

FOREIGN PATENT DOCUMENTS

| | | |
|---|---|---|
| EP | 2238926 | 10/2010 |
| EP | 2856955 | 4/2015 |
| GB | 2455343 | 6/2009 |
| JP | 62-292146 | 12/1987 |
| JP | H06-304127 | 11/1994 |
| JP | 2002-209835 | 7/2002 |
| JP | 2004180858 | 7/2004 |
| JP | 2005-131373 | 5/2005 |
| JP | 2007-325721 | 12/2007 |
| JP | 2008-006277 | 1/2008 |
| JP | 2009-291372 | 12/2009 |
| JP | 2010-502374 | 1/2010 |
| JP | 2011-010671 | 1/2011 |
| JP | 2014-014461 | 1/2014 |
| WO | 9848688 | 11/1998 |
| WO | 2005099558 | 10/2005 |
| WO | 2013176167 | 11/2013 |

OTHER PUBLICATIONS

"Search Report of Europe Counterpart Application", dated Jun. 29, 2017, p. 1-p. 9.

"Office Action of U.S. Appl. No. 15/275,473", dated Jan. 2, 2019, p. 1-p. 51.

"Office Action of Janpan Counterpart Application," dated Aug. 31, 2017, with English translation thereof, p. 1-p. 5.

"Written Opinion of the International Searching Authority (Form PCT/ISA/237)" of PCT/JP2015/059353, dated Jun. 23, 2015, pp. 1-6, in which three of the listed references (WO2013/176167, JP2007-325721 and JP2005-131373) were cited.

"Partial Search Report of European Counterpart Application", dated Feb. 13, 2017, p. 1-p. 6, in which the listed references were cited.

"Office Action of European Counterpart Application" dated Apr. 24, 2018, p. 1-p. 5.

"Search Report of Europe Counterpart Application", dated May 18, 2017, p. 1-p. 12.

"Search Report of Europe Counterpart Application", dated Apr. 26, 2019, p. 1-p. 8.

SURGICAL APPARATUS FOR ENDOSCOPE

CROSS-REFERENCE TO RELATED APPLICATIONS

This application is a Continuation of PCT International Application No. PCT/JP2015/077585 filed on Sep. 29, 2015, which claims priority under 35 U.S.C. § 119(a) to U.S. Provisional Application No. 62/057,525 filed on Sep. 30, 2014. Each of the above applications is hereby expressly incorporated by reference, in their entirety, into the present application.

BACKGROUND OF THE INVENTION

1. Field of the Invention

The present invention relates to a surgical apparatus for an endoscope, and particularly, relates to a surgical apparatus for an endoscope that can operate an endoscope and a treatment tool inserted through two insertion passages provided in an outer tube in an interlocking manner.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, is widely performed. In the endoscopic surgery, a plurality of holes are made in a patient's body wall, an endoscope is inserted into a body cavity from one hole of them, and a treatment tool is inserted into the body cavity from another hole. Then, treatment of a living body tissue is performed with the treatment tool while observing the living body tissue within the body cavity with the endoscope.

Generally, in the endoscopic surgery, one or a plurality of treatment tools are used simultaneously with the endoscope. Therefore, since it is difficult for one operator to simultaneously operate the endoscope and the plurality of treatment tools, for example, a task where the operator operates treatment tools using both hands while making an assistant called an endoscopic technician operate the endoscope is normally performed.

In this way, in the endoscopic surgery, it is general that the operator's hands are bound by the operation of the treatment tool, and the operation of the endoscope is performed by the assistant. Therefore, in a case where the observation position of the endoscope is changed, the operator should serially give instructions to the assistant. Hence, the task of correctly directing the orientation of the endoscope to a direction desired by the operator is difficult, and stress is likely to be imposed on the operator. Additionally, since the assistant performs an operation after the operator issues an instruction, there is a tendency that surgery time is likely to be prolonged. Additionally, the assistant should operate the endoscope so as not to interfere with an operator's procedure, and the operation is likely to become complicated.

In contrast, the applicant of the present application suggests a technique in which an endoscope and a treatment tool are combined together by an outer tube, and if the treatment tool is moved forward and backward, the endoscope is also moved forward and backward in an interlocking manner with this movement of the treatment tool (refer to WO2013/176167A). Specifically, the outer tube that guides an insertion part of the endoscope and an insertion part of the treatment tool into a body cavity includes a tubular outer tube body that is inserted in a state where the insertion part of the endoscope and the insertion part of the treatment tool are made to be parallel to each other. An interlocking member that is movable forward and backward in an axial direction and has an endoscope coupling part and a treatment tool-coupling part is provided inside the outer tube body. The insertion part of the endoscope and the insertion part of the treatment tool are held by the respective coupling parts of the interlocking member in a state where the insertion parts are made to be parallel to each other. If the insertion part of the treatment tool is moved in the axial direction, the insertion part of the endoscope also moves in the axial direction in an interlocking manner with this movement. Accordingly, the number of the holes made in the patient's body wall can be reduced, the invasion to the patient can be suppressed, and the visual field of the endoscope can be easily changed while an operator operates the treatment tool without asking for an assistant's help.

SUMMARY OF THE INVENTION

However, in the technique that the applicant of the present application has suggested previously, at the time of mounting of the endoscope when the insertion part of the endoscope is coupled to the endoscope-coupling part of the interlocking member by inserting the endoscope through the outer tube, the position of the interlocking member within the outer tube body cannot be seen. For that reason, to which position of the insertion part of the endoscope the endoscope-coupling part is coupled cannot be clearly ascertained.

Hence, mounting work of the endoscope onto the outer tube may be completed in a state where the endoscope-coupling part is coupled to a position that is excessively close to a distal end side of the insertion part of the endoscope. In that case, during treatment, when the endoscope and the treatment tool are interlocked with each other by the interlocking member and move to a base end side, a situation where the distal end of the insertion part of the endoscope enters the inside of the outer tube may occur.

If the distal end of the insertion part of the endoscope enters the inside of the outer tube, a portion of an observation visual field of the observation part is blocked by the outer tube and a substantial range of the observation visual field becomes narrow. Therefore, it becomes difficult to perform the treatment.

The invention has been made in view of such circumstances, and an object thereof is to provide a surgical apparatus for an endoscope that can appropriately and easily perform mounting work of an endoscope onto an outer tube.

In order to achieve the above object, a surgical apparatus for an endoscope according to an aspect of the invention is a surgical apparatus for an endoscope comprising an endoscope having an observation window at a distal end thereof; a treatment tool having a treatment part at a distal end thereof; and an outer tube that passes through a body wall, is inserted into a body cavity, and guides the endoscope and the treatment tool into the body cavity. The outer tube includes an outer tube body having a distal end, a base end, and a longitudinal axis, a first distal end opening and a second distal end opening provided at the distal end of the outer tube body, a first base end opening and a second base end opening provided at the base end of the outer tube body, an endoscope insertion passage that is provided along the longitudinal axis of the outer tube body, allows the first distal end opening and the first base end opening to communicate with each other therethrough, and allows the endoscope to be inserted therethrough so as to be movable forward and backward, a treatment tool insertion passage that is provided along the longitudinal axis of the outer tube body, allows the second distal end opening and the second base end opening to communicate with each other therethrough, and allows the treatment tool to be inserted therethrough so as to be movable forward and backward, an interlocking member that has an endoscope-coupling part coupled to the endoscope inserted through the endoscope insertion passage, and a treatment tool-coupling part coupled to the treatment tool inserted through the treatment tool insertion passage and is movable forward and backward inside the outer tube body, a first stopper that is provided inside the outer tube body and restricts movement of the interlocking member to the distal end side of the outer tube body, and a second stopper that is provided inside the outer tube body and restricts movement of the interlocking member to the base end side of the outer tube body. The endoscope has a positioning part at a position apart by at least Lt+L1 from a distal end of the endoscope toward a base end side thereof when a movement distance of the interlocking member when the interlocking member moves from a first position where movement thereof to the distal end side of the outer tube body is restricted by the first stopper to a second position where movement thereof to the base end side of the outer tube body is restricted by the second stopper is defined as L1 and a length of the outer tube body in a longitudinal axis direction is defined as Lt.

According to the invention, when the endoscope is mounted on the outer tube by inserting the endoscope through the endoscope insertion passage of the outer tube, the positioning part of the insertion part of the endoscope is matched with the position of the base end of the outer tube. Thus, irrespective of the operator and irrespective of every use (mounting), the endoscope insertion part can be easily positioned at a predetermined position with respect to the outer tube.

In this case, the insertion part of the endoscope protrudes by at least the movement distance L1 or more of the interlocking member from the distal end of the outer tube. For that reason, at the time of the treatment after the mounting of the endoscope and the treatment tool onto the outer tube, even in a case where the endoscope and the treatment tool are interlocked with each other by the interlocking member and moved to the second position where the movement of the interlocking member to the base end side is restricted, the distal end of the insertion part of the endoscope does not enter the inside of the outer tube. Hence, the endoscope-coupling part of the interlocking member is in the state of being coupled to the insertion part of the endoscope at a suitable position, and the mounting of the endoscope to the outer tube is appropriately performed.

Additionally, since it is possible to recognize, during treatment, that the interlocking member reaches the first position from the positioning part of the endoscope being located at the base end of the outer tube or abutting against the base end of the outer tube, excellent situation recognition can be made. Treatment performance is improved by virtue of the excellent situation recognition.

In the surgical apparatus for an endoscope according to the aspect of the invention, it is possible to adopt an aspect in which the positioning part has an abutment part that abuts against a base end surface of the outer tube body from the base end side.

According to this aspect, the mounting of the endoscope onto the outer tube can be appropriately performed simply by making the abutment part of the endoscope insertion part abut against the base end of the outer tube at the time of the mounting of the endoscope onto the outer tube.

In the surgical apparatus for an endoscope according to the aspect of the invention, it is possible to adopt an aspect in which the abutment part is an operating part gripped by an operator who operates the endoscope.

According to this aspect, the abutment part can also be used for operation, such as the forward and backward movement operation of the endoscope, and it is also possible to make provision of the abutment part and the operating part unnecessary.

In the surgical apparatus for an endoscope according to the aspect of the invention, it is possible to adopt an aspect in which the operating part has a shaft part having a larger external diameter than the internal diameter of the first base end opening.

In the surgical apparatus for an endoscope according to the aspect of the invention, it is possible to adopt an aspect in which the shaft part has an outer peripheral surface in which at least one of an antislip shape or an antislip member is formed.

According to this aspect, in a case where the shaft part is made to serve also as the operating part of the endoscope, the operation of the endoscope is easily performed.

In the surgical apparatus for an endoscope according to the aspect of the invention, it is possible to adopt an aspect in which the positioning part is a marker that is formed on a surface of the endoscope and indicates a position apart by at least Lt+L1 from the distal end of the endoscope toward the base end side thereof.

According to this aspect, the positioning part can be simply provided.

In the surgical apparatus for an endoscope according to the aspect of the invention, it is possible to adopt an aspect in which the positioning part is provided at a position apart by Lt+L1 from the distal end of the endoscope toward the base end side thereof.

According to this aspect, at the time of the treatment after the mounting of the endoscope and the treatment tool onto the outer tube, in a case where the endoscope and the treatment tool are interlocked with each other by the interlocking member and moved to the second position where the movement of the interlocking member to the base end side is restricted, the distal end of the endoscope insertion part comes to a position coinciding with the position of the distal end of the outer tube. Hence, this aspect is an aspect in which the amount of protrusion of the insertion part of the endoscope from the distal end of the outer tube becomes the minimum in a case where the insertion part of the endoscope is kept from entering the inside of the outer tube.

Moreover, according to this aspect, the positioning part is provided at the position apart exactly by Lt+L1 from the distal end of the endoscope to the base end side. Therefore, the amount of protrusion of the endoscope from the distal end of the outer tube can be easily estimated simply by confirming the distance between the positioning part and the base end of the outer tube.

In the surgical apparatus for an endoscope according to the aspect of the invention, it is possible to adopt an aspect in which the interlocking member has a non-sensing region where the forward and backward movement of either the endoscope or the treatment tool does not interlock with the movement of the other and a sensing region where the forward and backward movement of either the endoscope or the treatment tool interlocks with the movement of the other.

According to this aspect, since the endoscope does not move forward and backward, for example, with respect to the forward and backward movement operation of the treatment tool in the non-sensing region, there is an advantage that a stable observation image can be obtained.

According to the invention, the mounting work of the endoscope onto the outer tube can be appropriately and easily performed.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
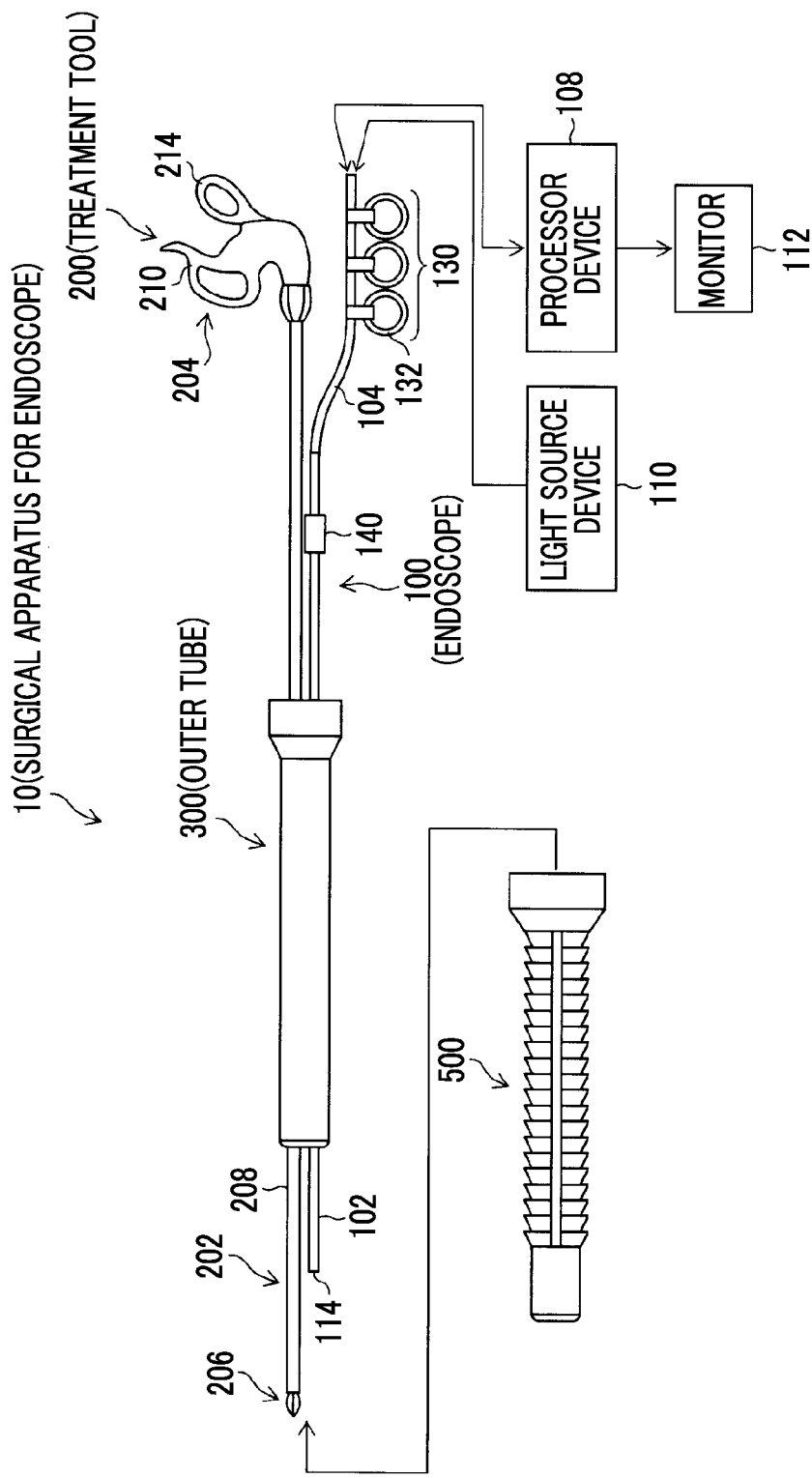
FIG. 1 is a schematic block diagram of a surgical apparatus for an endoscope according to the invention.

FIG. 1 is a schematic block diagram of a surgical apparatus for an endoscope according to the invention. As illustrated in FIG. 1, a surgical apparatus for an endoscope 10 includes an endoscope 100 that observes the inside of a patient's body cavity, a treatment tool 200 for examining or treating a diseased site within the patient's body cavity, an outer tube 300 that is inserted into a body wall and guides the endoscope 100 and the treatment tool 200 into the body cavity, and an exterior tube 500 fitted to the outer tube 300.

The endoscope 100 is, for example, a hard endoscope, such as a laparoscope, and includes an insertion part 102 (hereinafter referred to as "endoscope insertion part 102") that is inserted into a body cavity, and that has an outer peripheral part surrounded by an elongated hard tubular body, and a cable part 104 that is provided continuously with a base end side of the endoscope insertion part 102 and that has an outer peripheral part surrounded by an elongated flexible tubular body.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
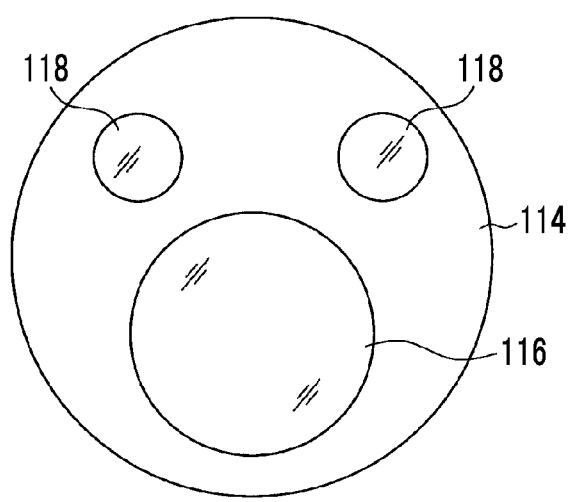
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and a solid image pickup element, such as a charge coupled device (CCD) image sensor or a complementary metal oxide semiconductor (CMOS) image sensor, which is disposed at an image pickup position of the objective lens, are disposed behind the observation window 116. A signal cable (not illustrated) connected to this solid image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pickup element, and is converted into electrical signals (image pickup signals), and the electrical signals are output to the processor device 108 via the signal cable and are converted into video signals. Then, the video signals are output to the monitor 112 connected to the processor device 108, and the observation image (endoscopic image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Hence, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

Addition, as illustrated in FIG. 1, the cable part 104 of the endoscope 100 is provided with a forward and backward movement operating part 130 for hooking the index finger of a right hand gripping an operating part 204 of the treatment tool 200, and performing a forward and backward movement operation of the endoscope 100 in a forward-backward direction of the endoscope 100.

The forward and backward movement operating part 130 is disposed at a position adjacent to the operating part 204 of the treatment tool 200, and has, for example, three hooking parts 132 of the same configuration. Each hooking part 132 is formed in an annular shape (ring shape) using elastic materials (for example, rubber materials), and has an opening of such a size that an index finger can pass therethrough.

Accordingly, an operator can pass the index finger of his/her right hand gripping the operating part 204 of the treatment tool 200, through any hooking part 132 of the forward and backward movement operating part 130 to perform the forward and backward movement operation of the endoscope 100, and can easily perform the operation of the treatment tool 200 and the forward and backward movement operation of the endoscope 100 only with his/her right hand. In addition, the endoscope 100 may not include the forward and backward movement operating part 130, and the detailed description of the forward and backward movement operating part 130 will be omitted.

Moreover, although the endoscope insertion part 102 of the endoscope 100 is provided with a larger-diameter part 140, the details thereof will be described below.

As illustrated in FIG. 1, the treatment tool 200 consists of, for example, forceps, and includes an elongated insertion part 202 (hereinafter referred to as a "treatment tool insertion part 202") that is inserted into a body cavity, an operating part 204 that is provided on the base end side of the treatment tool insertion part 202 and is gripped by an operator, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the outer tube 300 allows the endoscope insertion part 102 and the treatment tool insertion part 202, which are inserted thereinto from the base end side, to be inserted therethrough and delivered from the distal end side. By inserting the outer tube 300 into a body wall and having a base end side thereof disposed outside of the body and a distal end side thereof disposed within the body cavity, the endoscope insertion part 102 and the treatment tool insertion part 202 are guided into the body cavity with one outer tube 300. Additionally, the outer tube 300 includes an interlocking function of moving the endoscope insertion part 102 and the treatment tool insertion part 202 forward and backward in an interlocking manner as will be described below in detail. Accordingly, for example, the endoscope insertion part 102 can also be moved forward and backward by the forward and backward movement operation of only the treatment tool insertion part 202, and a suitable observation image can be obtained without performing the forward and backward movement operation of the endoscope insertion part 102. The details of the configuration and working of the outer tube 300 will be described below.

Figure 3:
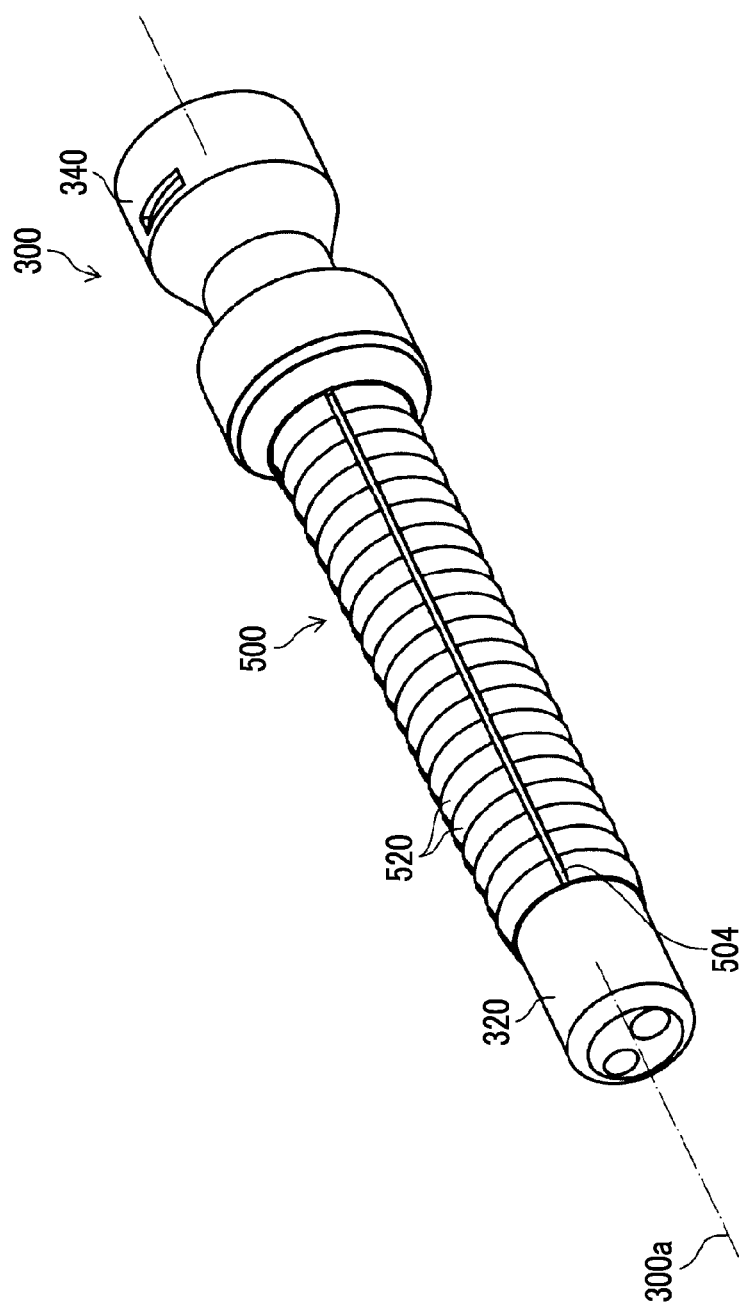
FIG. 3 is a perspective view illustrating a state where an exterior tube is fitted to an outer tube.

The exterior tube 500 illustrated in FIG. 1 is formed in a tubular shape, and as illustrated in FIG. 3, is externally fitted (sheathed) to and fixed to an outer peripheral surface of the outer tube 300 (a long tubular outer tube body 320 to be described below). Although detailed description is omitted, an outer peripheral part of the exterior tube 500 is provided with a number of lateral grooves 520 running along in a circumferential direction, and longitudinal grooves 504 running along an axial direction are provided, for example, in four places in the circumferential direction.

Accordingly, in a state where the outer tube 300 is inserted into a body wall together with the exterior tube 500, a number of the lateral grooves 520 of the exterior tube 500 restrict the forward and backward movement of the exterior tube 500 with respect to the body wall, and the longitudinal grooves in four places of the exterior tube 500 restrict the rotation of the exterior tube 500 in the circumferential direction (around a reference axis 300a) with respect to the body wall. Hence, unintended rotation or forward and backward movement of the outer tube 300 fixed to the exterior tube 500 with respect to the body wall is prevented.

Namely, if the outer tube 300 rotates around the reference axis 300a (around the axis) unintentionally with respect to the body wall or moves forward and backward in the direction (axial direction) of the reference axis 300a when the operation of the treatment tool 200, or the like is performed by inserting the endoscope insertion part 102 and the treatment tool insertion part 202 through the outer tube 300 after the outer tube 300 (long tubular outer tube body 320) is inserted into the body wall, there is a problem that the position of a distal end of the endoscope insertion part 102 may fluctuate and an observation visual field may fluctuate unintentionally. The exterior tube 500 prevents such unintended fluctuation of the observation visual field.

Figure 4:
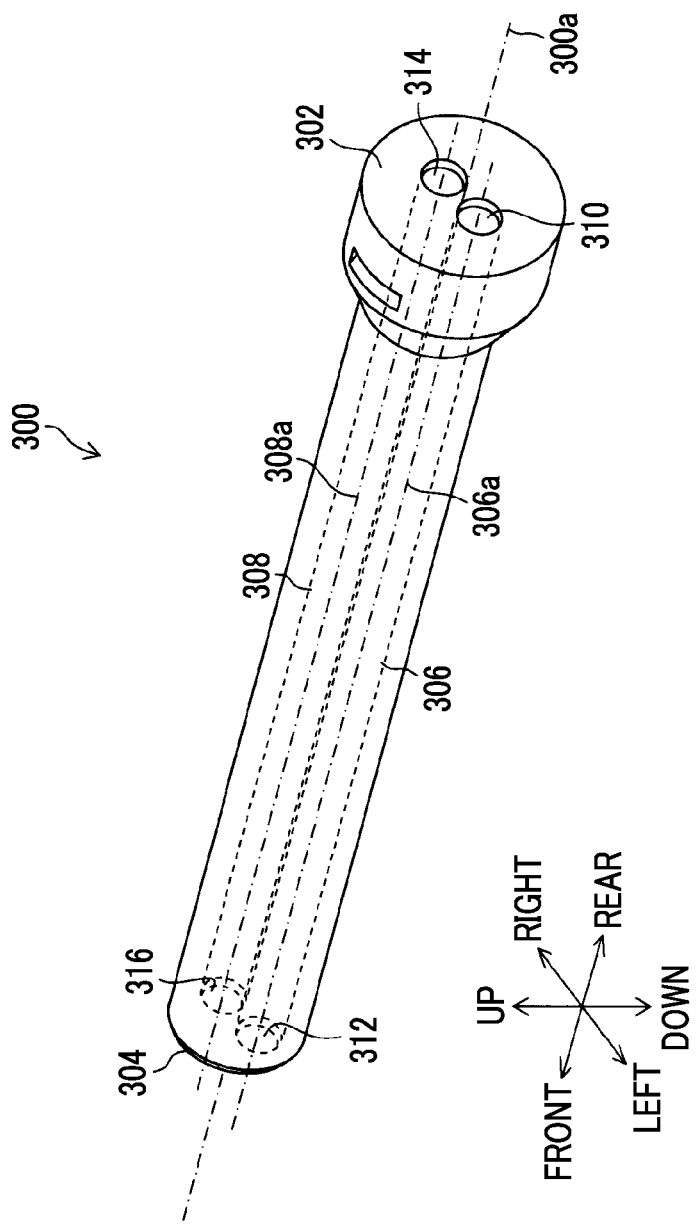
FIG. 4 is an external perspective view illustrating the outer tube.

FIG. 4 is an external perspective view illustrating the outer tube 300.

As illustrated in this drawing, the outer tube 300 has an elongated cylindrical shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a indicating a longitudinal axis that is a central axis of the outer tube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axis of the endoscope insertion part 102 and the central axis of the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are disposed on the same plane. However, a configuration in which the reference axis 300a, the endoscope insertion axis 306a, and the treatment tool insertion axis 308a are disposed on the same plane may not be adopted.

In addition, regarding the position and orientation of a space where the outer tube 300 has been disposed, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the outer tube 300 is provided with a first base end opening 310 that is a base end opening that allows the endoscope insertion part 102 to be inserted into the endoscope insertion passage 306 therethrough, and a second base end opening 314 that is base end opening that allows the treatment tool insertion part 202 to be inserted into the treatment tool insertion passage 308 therethrough.

The distal end surface 304 of the outer tube 300 is provided with a first distal end opening 312 that is a distal end opening that allows the endoscope insertion part 102 inserted into the endoscope insertion passage 306 to be delivered to the outside therethrough, and a second distal end opening 316 that is a distal end opening that allows the treatment tool insertion part 202 inserted into the treatment tool insertion passage 308 to be delivered to the outside therethrough.

Figure 5:
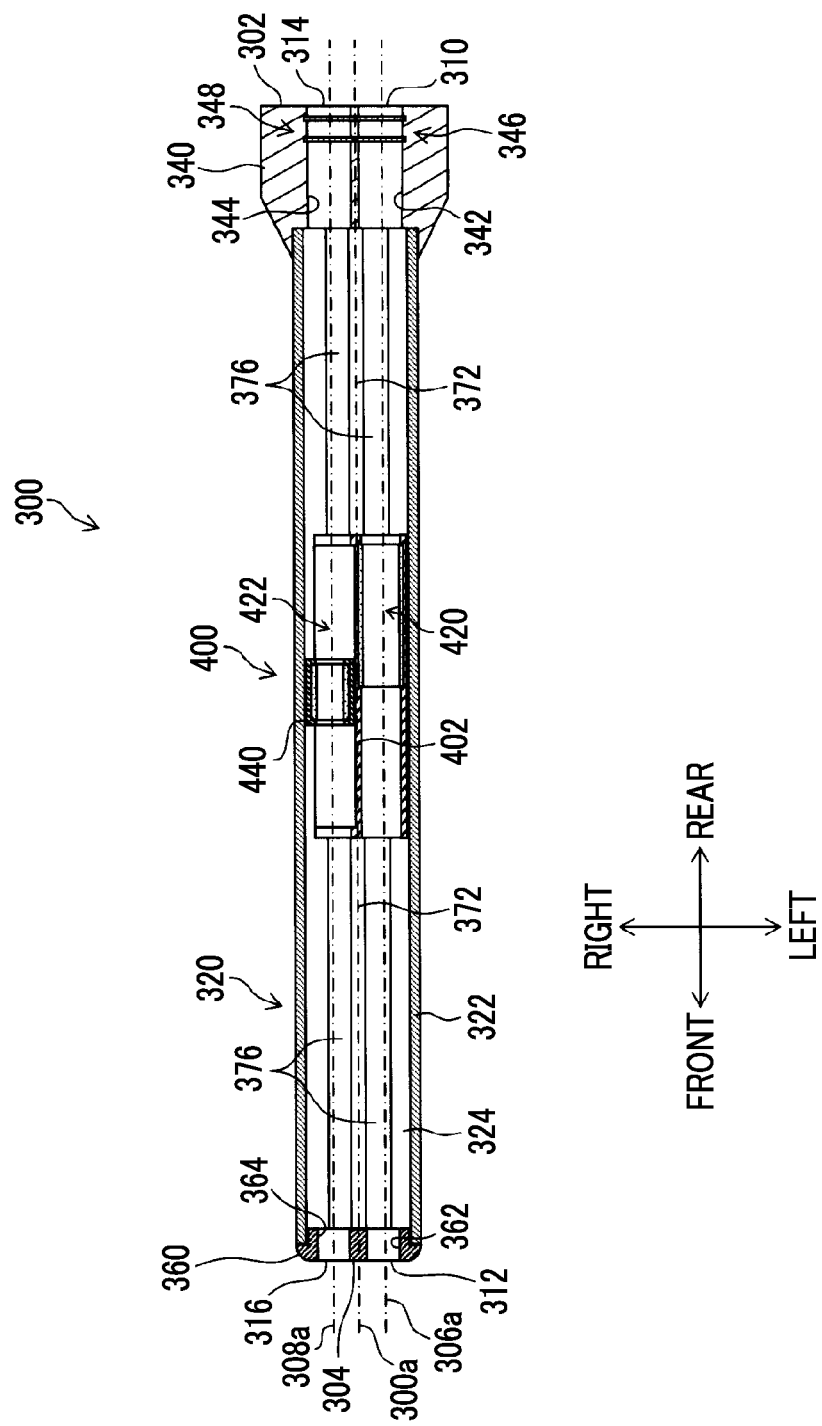
FIG. 5 is a cross sectional view illustrating the internal structure of the outer tube.

FIG. 5 is a cross sectional view illustrating the internal structure of the outer tube 300, and illustrates a cross section cut in a plane that includes the reference axis 300a and is orthogonal to an upward-downward direction (cut in a leftward-rightward direction along the reference axis 300a).

As illustrated in this drawing, the outer tube 300 has a long tubular outer tube body 320 that occupies substantially the entire area in the forward-backward direction, a base end cap 340 that is attached to a rear end (base end) of the outer tube 300, a distal end cap 360 that is attached to a distal end part, and a slider 400 that is one form of the interlocking member disposed inside the outer tube 300.

The long tubular outer tube body 320 is formed in an elongated cylindrical shape having the reference axis 300a as a central axis using hard resins, metals, or the like, and has an outer wall 322 that surrounds an outer periphery, and a cavity part 324 that penetrates from a base end of the long tubular outer tube body 320 to a distal end thereof.

The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the long tubular outer tube body 320 using hard resins, metals, or the like, and a rear end surface thereof constitutes the base end surface 302 of the outer tube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described first base end opening 310, and an opening of the through-hole 344 is equivalent to the above-described second base end opening 314.

Additionally, the through-holes 342 and 344 are provided with valve members 346 and 348. The valve members 346 and 348, for example, open only in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a distal end surface thereof constitutes the distal end surface 304 of the outer tube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described first distal end opening 312, and an opening of the through-hole 364 is equivalent to the second distal end opening 316.

In addition, the long tubular outer tube body 320, the base end cap 340, and the distal end cap 360 show one form of constituent members that constitutes the outer tube body of the outer tube 300, and the outer tube body is not limited to the above configuration. For example, the long tubular outer tube body 320 and the base end cap 340 or the long tubular outer tube body 320 and the distal end cap 360 may be integrally formed, or may be integrally formed in their entirety.

Additionally, the outer tube body may have the following configurations.

Namely, the outer tube body has a distal end, a base end, and a longitudinal axis, and includes a first distal end opening and a second distal end opening equivalent to the above-described first distal end opening 312 and second distal end opening 316 that are provided at the distal end of the outer tube body, and a first base end opening and a second base end opening equivalent to the above-described first base end opening 310 and the second base end opening 314 that are provided at the base end of the outer tube body. The outer tube body just has to include an endoscope insertion passage and a treatment tool insertion passage equivalent to the above-described endoscope insertion passage 306 and treatment tool insertion passage 308 that are provided along the longitudinal axis of the outer tube body, that is, the endoscope insertion passage that communicates with the first distal end opening and the first base end opening and allows the endoscope 100 to be inserted therethrough so as to be movable forward and backward, and the treatment tool insertion passage that communicates with the second distal end opening and the second base end opening and allows the treatment tool 200 to be inserted therethrough so as to be movable forward and backward.

The slider 400 is housed within (the cavity part 324) the long tubular outer tube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a non-sensing region where the forward and backward movement of either the endoscope insertion part or the treatment tool insertion part in the forward-backward direction (axial direction) does not interlock with the movement of the other and a sensing region where the forward and backward movement of either the endoscope insertion part or the treatment tool insertion part interlocks with the movement of the other. That is, the endoscope insertion part 102 is adapted to interlock with the forward and backward movement of the treatment tool insertion part 202 in the axial direction with play by the slider 400.

Figure 6:
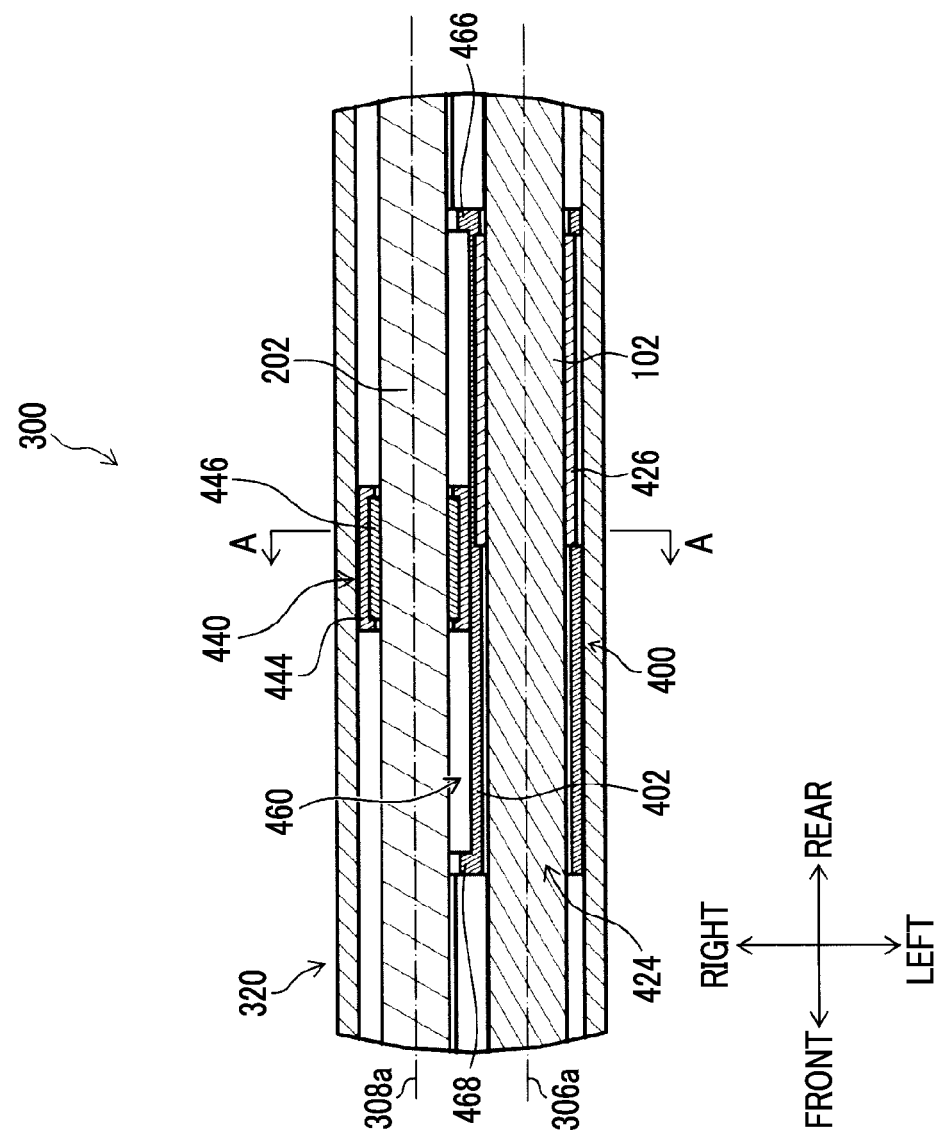
FIG. 6 is an enlarged cross sectional view illustrating a portion of FIG. 5 in an enlarged manner.
Figure 7:
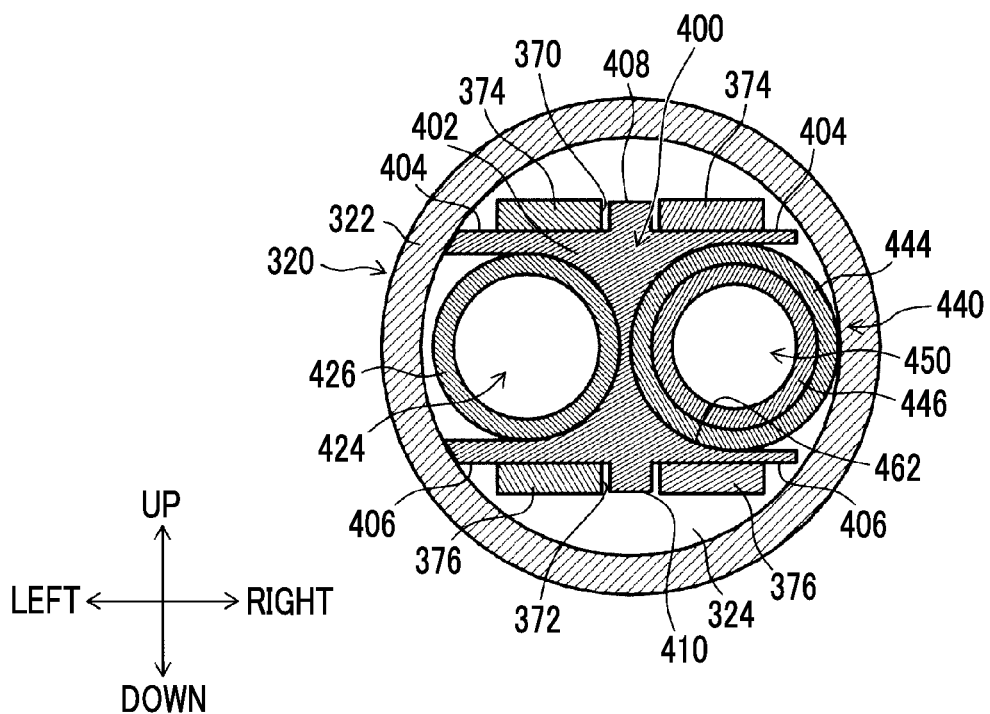
FIG. 7 is a cross sectional view as viewed from arrow A-A in FIG. 6.

FIG. 6 is an enlarged cross sectional view illustrating a portion, in which the slider 400 is disposed in FIG. 5, in an enlarged manner, and illustrates a state where the endoscope insertion part 102 and the treatment tool insertion part 202 are inserted through the endoscope insertion passage 306 and the treatment tool insertion passage 308, respectively. FIG. 7 is a cross sectional view as seen from arrow A-A in FIG. 6.

Figure 8:
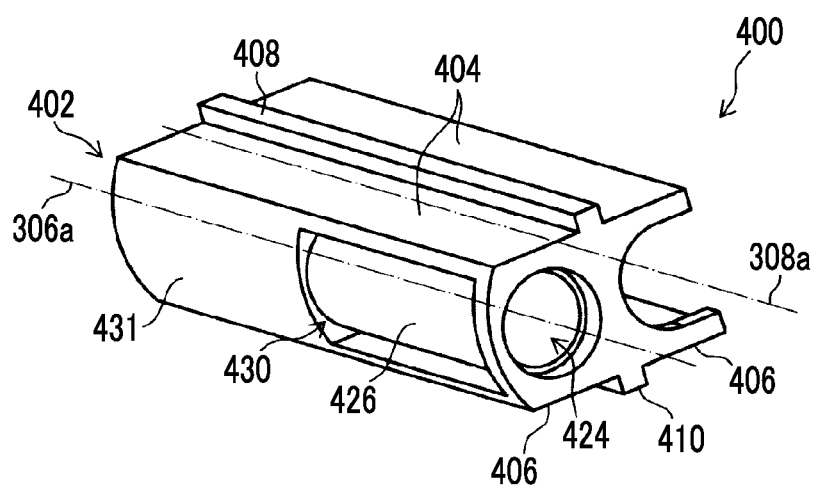
FIG. 8 is a perspective view illustrating a slider (interlocking member) from the rear upper left side.
Figure 9:
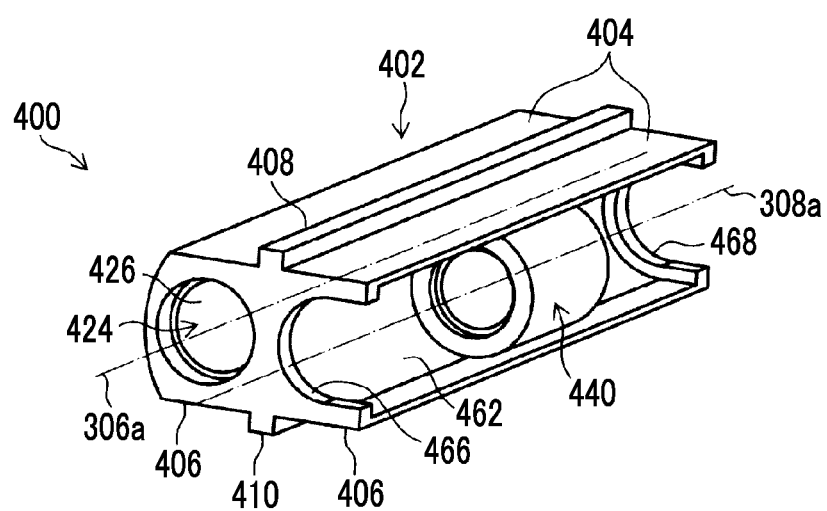
FIG. 9 is a perspective view illustrating the slider (interlocking member) from the rear upper right side.

Additionally, FIGS. 8 and 9 are respectively perspective views illustrating the slider 400 from the rear upper left and from the rear upper right.

As illustrated in these drawings, the slider 400 has a slider body 402 that holds components of the slider 400. As illustrated in FIG. 7, protruding strips 408 and 410 that extend in the direction (forward-backward direction) of the reference axis 300a are formed on a flat upper surface 404 (refer to FIGS. 8 and 9) and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360 and illustrated in FIG. 7, are respectively supported by an upper part and a lower part within the long tubular outer tube body 320, and guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the long tubular outer tube body 320, and the upper surface 404 and the lower surface 406 are disposed in a state where these surfaces contacted or approached the guide plates 374 and 374 and the guide plates 376 and 376.

Accordingly, the slider 400 is supported so as to be movable forward and backward in the forward-backward direction within the long tubular outer tube body 320, and is supported in a state where the movement of the slider in the upward-downward direction and in the leftward-rightward direction and the rotation of the slider in all directions (directions around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 disposed within the long tubular outer tube body 320, and may be formed in the outer wall 322 of the long tubular outer tube body 320 or may be formed by other configurations.

Additionally, the slider 400, as illustrated in FIG. 5, has a left endoscope-coupling part 420 that is coupled to (engaged with) the endoscope insertion part 102, and a right treatment tool-coupling part 422 that is coupled to (engaged with) the treatment tool insertion part 202.

The endoscope-coupling part 420 provided on the left side of the slider body 402 secures a space serving as the endoscope insertion passage 306, within the long tubular outer tube body 320. Additionally, the endoscope-coupling part 420, as illustrated in FIG. 6, includes a through-hole 424 (refer to FIGS. 7, 8, and 9) into which the endoscope insertion part 102 is inserted, and a pressure-contact member 426 that is fixed to the through-hole 424 and is brought into pressure contact with the outer peripheral surface (side surface) of the endoscope insertion part 102 inserted through the endoscope insertion passage 306.

The pressure-contact member 426 is formed in a cylindrical shape using elastic materials, such as elastic rubber, as illustrated in FIGS. 7 and 8, and is fitted into up to a position coaxial with the through-hole 424 of the slider body 402 from an opening 430 formed on a left side surface 431 of the slider body 402 and fixed to the slider body 402, as illustrated in FIG. 8.

Accordingly, when the endoscope insertion part 102 has been inserted through the endoscope insertion passage 306, as illustrated in FIG. 6, the endoscope insertion part 102 is inserted through the through-hole 424, and the pressure-contact member 426 is brought into pressure contact with (engaged with) the outer peripheral surface of the endoscope insertion part 102. Accordingly, the central axis of the endoscope insertion part 102 is disposed coaxially with the endoscope insertion axis 306a.

The endoscope insertion part 102 and the slider 400 (slider body 402) are coupled to (engaged with) each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupling part 422 provided on the right side of the slider body 402 as illustrated in FIG. 5, as illustrated in FIG. 6, includes a sleeve 440 (refer to FIGS. 7 and 9) that is coupled to the treatment tool insertion part 202, and a guide part 460 that guides the sleeve 440 so as to be movable forward and backward in the forward-backward direction.

The sleeve 440, as illustrated in FIG. 7, includes a sleeve body 444 (frame body) formed in a cylindrical shape, and a pressure-contact member 446 fixed to the inside of the sleeve body 444. The pressure-contact member 446 is formed in a cylindrical shape using elastic materials, such as elastic rubber.

Accordingly, when the treatment tool insertion part 202 has been inserted through the treatment tool insertion passage 308, as illustrated in FIG. 6, the treatment tool insertion part 202 is inserted through the inside (the through-hole 450 of FIG. 7) of the pressure-contact member 446, the pressure-contact member 446 is brought into pressure contact with (engaged with) the outer peripheral surface of the treatment tool insertion part 202. Accordingly, the central axis of the treatment tool insertion part 202 is disposed coaxially with the treatment tool insertion axis 308*a*.

The treatment tool insertion part 202 and the sleeve 440 are coupled to each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupling part 422, as illustrated in FIGS. 7 and 9, is formed by a space surrounded by a guide surface 462 of the slider body 402 that extends in the direction of the reference axis 300*a* (treatment tool insertion axis 308*a*), within the cavity part 324 of the long tubular outer tube body 320, and an inner peripheral surface of the long tubular outer tube body 320. The sleeve 440 is housed and disposed in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIGS. 6 and 9, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 disposed in the space of the guide part 460 moves forward and backward in the forward-backward direction.

Hence, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

The working of the slider 400 configured as described above will be described together with the operation when the treatment of a diseased site within a patient's body cavity is performed using the surgical apparatus for an endoscope 10.

Figure 13:
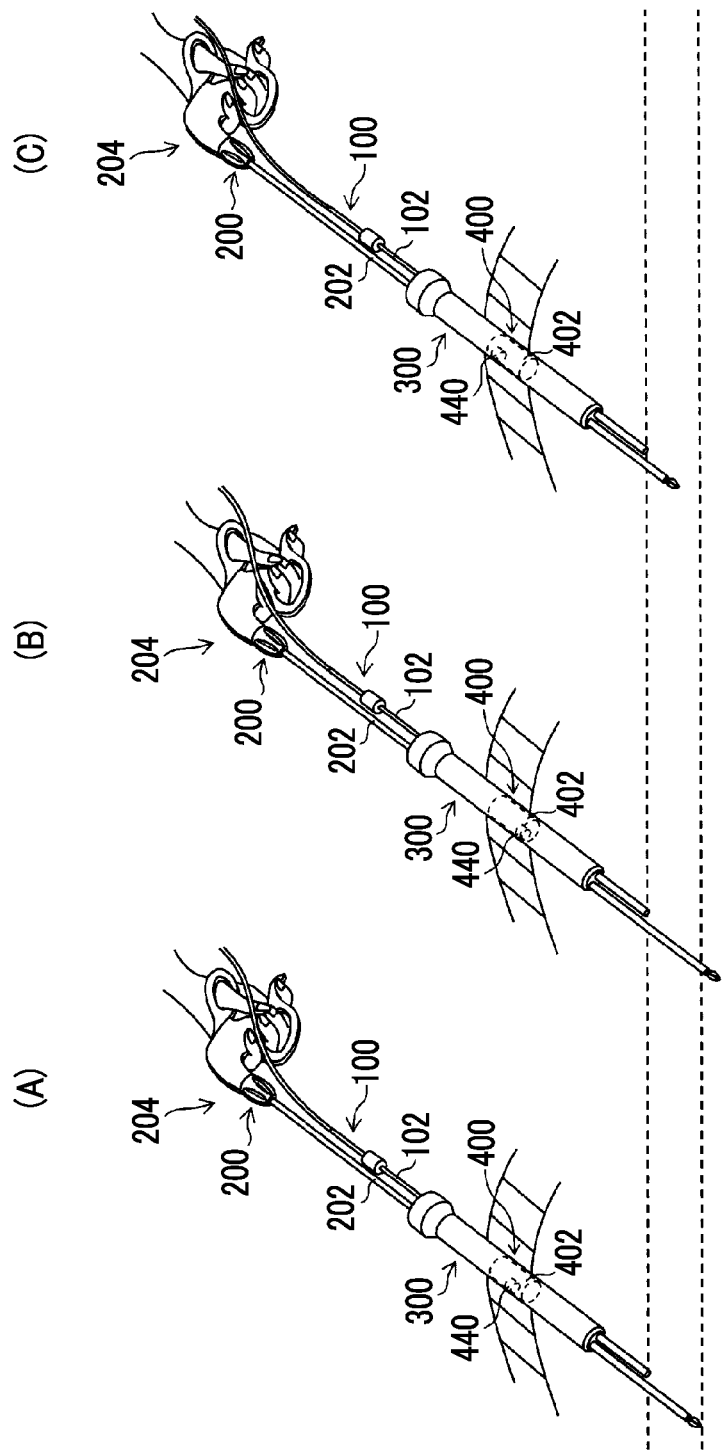
FIG. 13 is an explanatory view illustrating a state of the operation when the treatment of a diseased site within a patient's body cavity is performed using the surgical apparatus for an endoscope.
Figure 14:
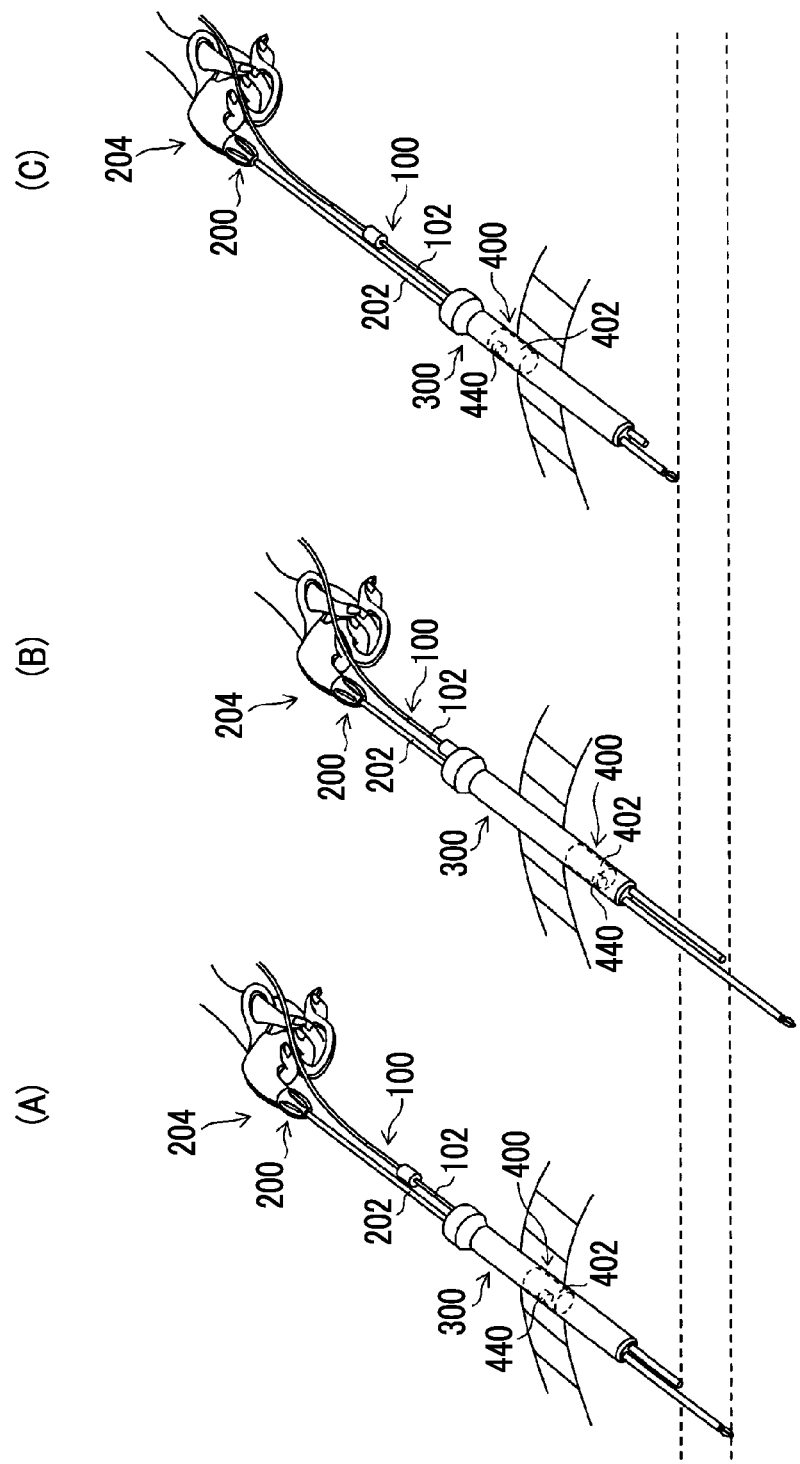
FIG. 14 is an explanatory view illustrating a state of the operation when the treatment of the diseased site within the patient's body cavity is performed using the surgical apparatus for an endoscope.

First, as illustrated in (A) part of FIG. 13, after the outer tube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the outer tube 300, and the endoscope insertion part 102 and the treatment tool insertion part 202 are mounted on the outer tube 300. In this case, the endoscope insertion part 102 is coupled to the slider body 402 of the slider 400, and the treatment tool insertion part 202 is coupled to the sleeve 440 of the slider 400. In addition, although the exterior tube 500 is not illustrated in FIG. 13, and FIG. 14 illustrated therebelow, the exterior tube 500 is fitted to the outer tube 300 as illustrated in FIG. 3. However, it is also possible to use the outer tube 300 without fitting the exterior tube 500 thereto. Additionally, the forward and backward movement operating part 130 of the endoscope 100 is also omitted in the drawings.

Figure 10:
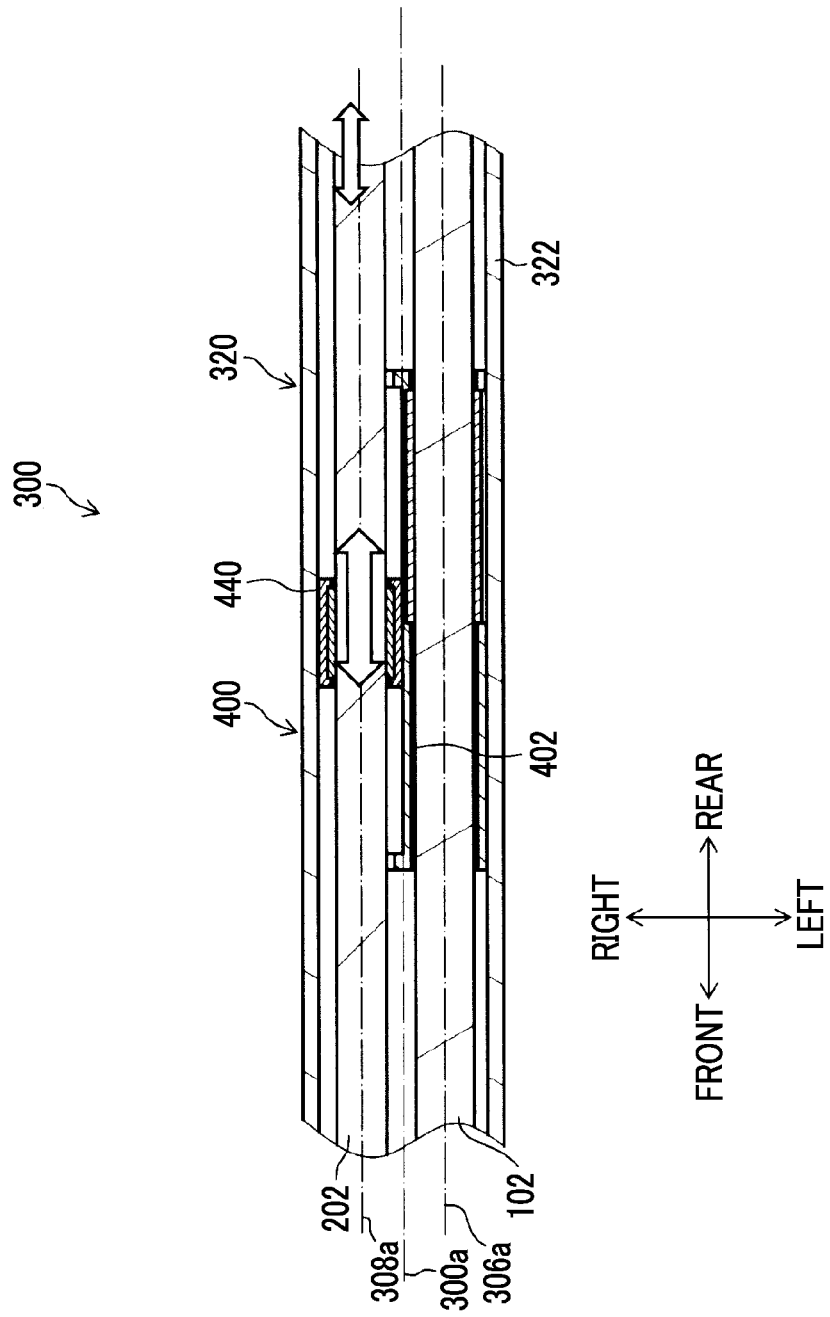
FIG. 10 is an explanatory view used for the description of the working of the slider (interlocking member).

Supposing the state of (A) part of FIG. 13 is a state where the sleeve 440 reaches neither the front end nor the rear end of the movable range thereof with respect to the slider body 402 (guide part 460) as illustrated in FIG. 10, and if an operator minutely moves the treatment tool insertion part 202 forward with his/her hand that is gripping the operating part 204 of the treatment tool 200, the slider body 402 does not move with respect to the outer tube 300 (long tubular outer tube body 320), but only the sleeve 440 moves forward with respect to the slider body 402 within the movable range thereof with respect to the slider body 402. For that reason, with respect to the forward movement of the treatment tool insertion part 202 until the sleeve 440 reaches the front end of the movable range thereof with respect to the slider body 402, as illustrated in (B) part of FIG. 13, only the treatment tool insertion part 202 moves forward in a state where the endoscope insertion part 102 is stationary. That is, the slider 400 has the non-sensing region where the endoscope insertion part 102 does not interlock with the forward and backward movement of the treatment tool insertion part 202, and the forward movement operation of the treatment tool 200 at this time becomes a forward and backward movement operation of the slider 400 in the non-sensing region.

Similarly, supposing the state of (A) part of FIG. 13 is a state where the sleeve 440 reaches neither the front end nor the rear end of the movable range thereof with respect to of the slider body 402 (guide part 460) as illustrated in FIG. 10, and if the operator minutely moves the treatment tool insertion part 202 backward with his/her hand that is gripping the operating part 204 of the treatment tool 200, the slider body 402 does not move with respect to the outer tube 300 (long tubular outer tube body 320), but only the sleeve 440 moves backward with respect to the slider body 402 within the movable range thereof with respect to the slider body 402. For that reason, with respect to the backward movement of the treatment tool insertion part 202 until the sleeve 440 reaches the rear end of the movable range thereof with respect to the slider body 402, as illustrated in (C) part of FIG. 13, only the treatment tool insertion part 202 moves backward in a state where the endoscope insertion part 102 is stationary. That is, the backward movement operation of the treatment tool 200 at this time becomes a backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation image to be displayed on the monitor 112 does not vary, and the size of a target to be observed can be prevented from fluctuating according to minute displacement of the treatment tool 200. Accordingly, a sense of perspective can be suitably maintained, and a stable observation image can be provided.

Figure 11:
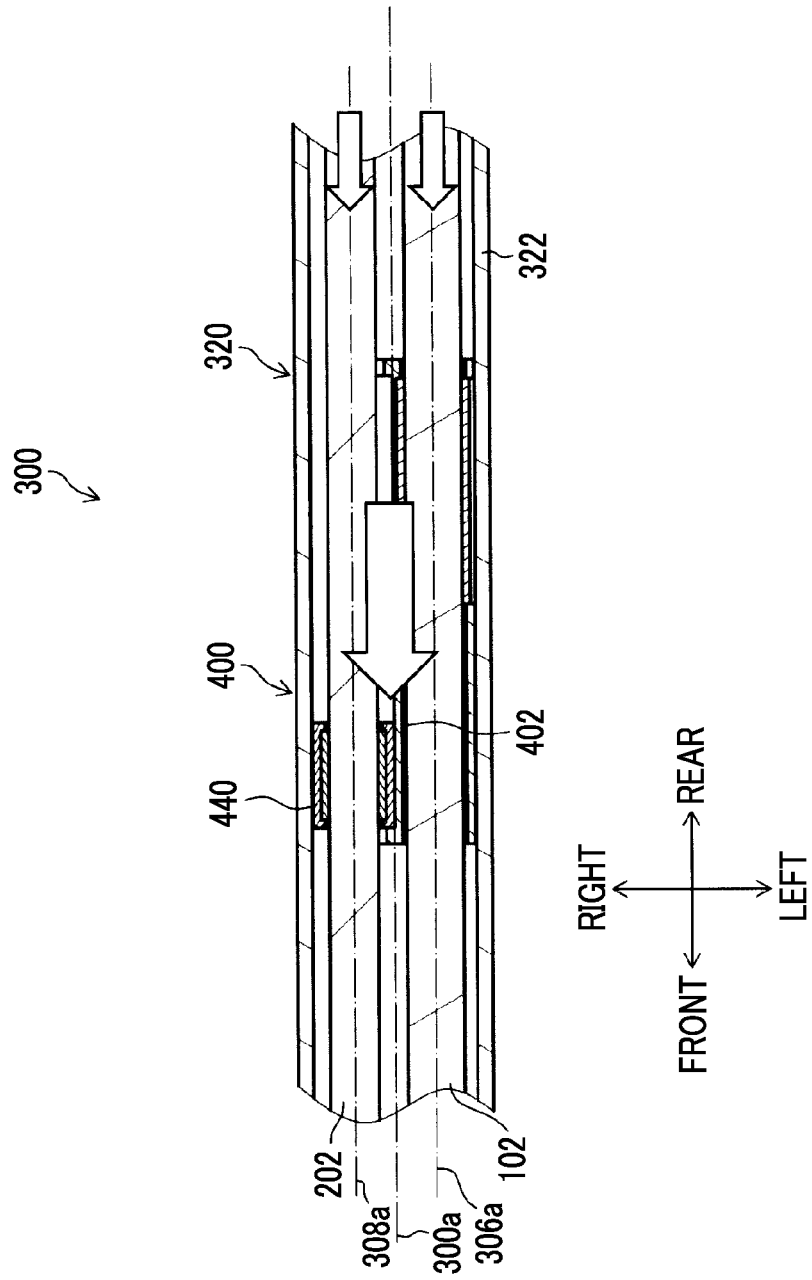
FIG. 11 is an explanatory view used for the description of the working of the slider (interlocking member).

Meanwhile, if the operator greatly moves the treatment tool insertion part 202 forward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the front end of the movable range thereof with respect to the slider body 402 as illustrated in FIG. 11 is brought into after the forward movement of the sleeve 440 of the slider 400 in the non-sensing region until it abuts against the front end of the movable range. Then, if the treatment tool insertion part 202 further moves forward, the sleeve 440 and the slider body 402 moves forward with respect to the long tubular outer tube body 320 together with the treatment tool insertion part 202. As a result, the endoscope insertion part 102 moves forward in an interlocking manner with the treatment tool insertion part 202. For that reason, with respect to the forward movement of the treatment tool insertion part 202 after the sleeve 440 reaches the front end of the movable range thereof with respect to the slider body 402, the endoscope insertion part 102 moves forward in an interlocking manner with the treatment tool insertion part 202 as illustrated in (B) part of FIG. 14, compared to the state of (A) part of FIG. 14 illustrating the same state as (A) part of FIG. 13. That is, the slider 400 has the sensing region where the endoscope insertion part 102 interlocks with the forward and backward movement of the treatment tool insertion part 202, and the forward movement operation of the treatment tool 200 at this time becomes a forward movement operation of the slider 400 in the sensing region.

Figure 12:
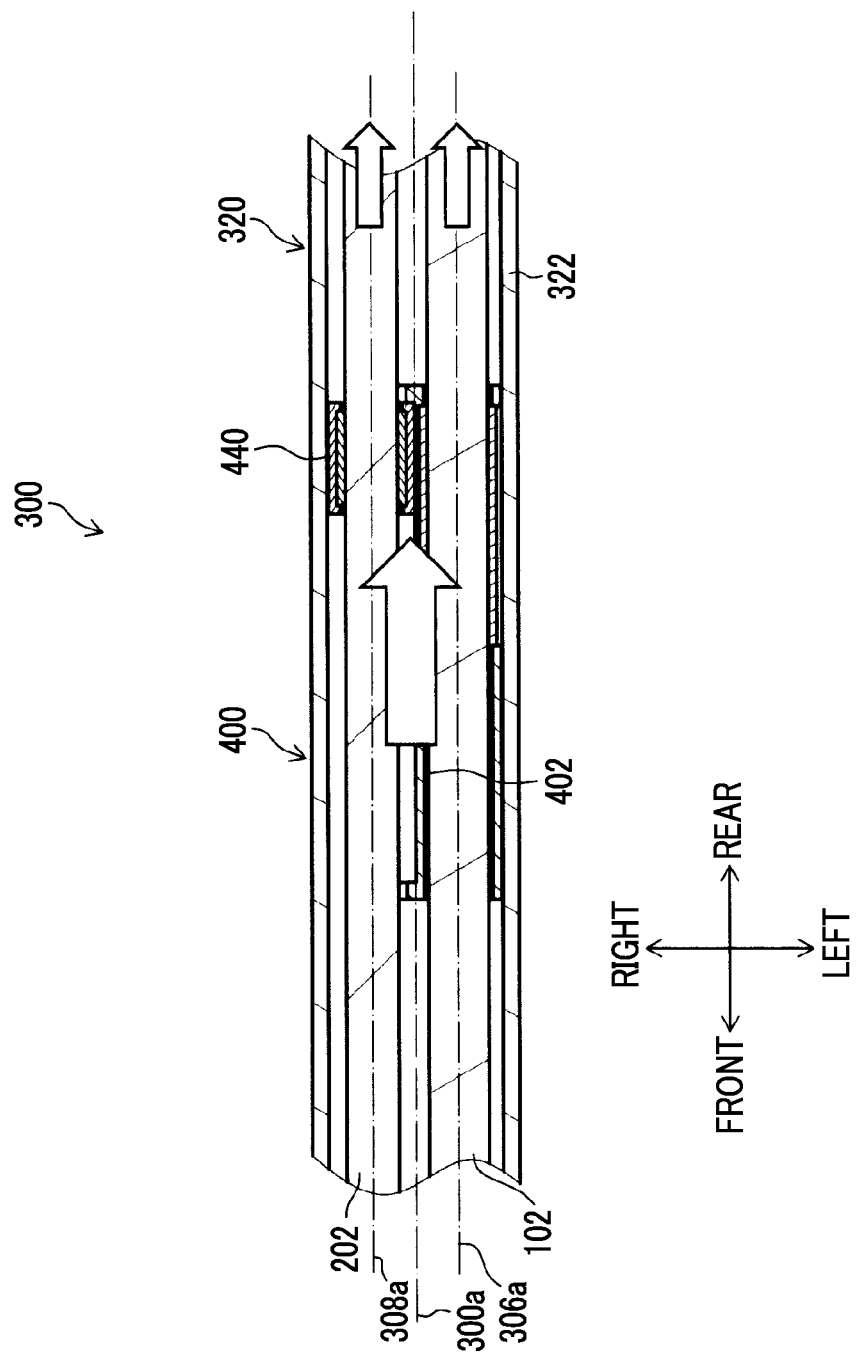
FIG. 12 is an explanatory view used for the description of the working of the slider (interlocking member).

Similarly, if the operator greatly moves the treatment tool insertion part 202 backward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the rear end of the movable range thereof with respect to the slider body 402 as illustrated in FIG. 12 is brought into after the backward movement of the sleeve 440 of the slider 400 in the non-sensing region until it abuts against the rear end of the movable range. Then, if the treatment tool insertion part 202 further moves backward, the sleeve 440 and the slider body 402 moves backward with respect to the long tubular outer tube body 320 together with the treatment tool insertion part 202. As a result, the endoscope insertion part 102 moves backward in an interlocking manner with the treatment tool insertion part 202. For that reason, with respect to the backward movement of the treatment tool insertion part 202 after the sleeve 440 reaches the rear end of the movable range thereof with respect to the slider body 402, as illustrated in (C) part of FIG. 14, the endoscope insertion part 102 moves backward in an interlocking manner with the treatment tool insertion part 202. That is, the backward movement operation of the treatment tool 200 at this time becomes a backward movement operation of the slider 400 in the sensing region.

Hence, since the endoscope 100 moves forward and backward with respect to a large forward and backward movement operation of the treatment tool 200, that is, the forward and backward movement operation thereof in the sensing region, the range of an observation image to be displayed on the monitor 112 is continuously changed so as to follow the forward and backward movement of the treatment tool 200. Accordingly, since the size of a target to be observed varies according to the operation of the treatment tool 200, the operator can simply obtain a desired image.

As described above, in a case where the displacement of the treatment tool insertion part 202 in the axial direction is large (in a case where a large amplitude of forward and backward movement has been performed) when an operator has moved the treatment tool insertion part 202 forward and backward in the axial direction, the endoscope insertion part 102 also moves in an interlocking manner forward, backward, up, down, right, and left. Thus, the visual field, orientation, and the like of the endoscope 100 can be changed as intended by an operator. Additionally, the visual field is always given to pick up an image of the distal end of the treatment tool, and consequently, an image that is optimal for treatment is automatically provided. In a case where it is desired to check sites other than a site to be treated, the checking can be performed by moving the treatment tool insertion part 202, and an operator can perform operations as desired. Hence, an assistant (endoscopic technician) who operates the endoscope 100 apart from the operator can be made unnecessary, and a troublesome condition in which the operator should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, the size of a target to be observed within an observation image can be prevented from fluctuating unnecessarily, a sense of perspective can be suitably maintained, and a stable observation image can be provided.

Next, positioning means when the endoscope insertion part 102 of the endoscope 100 is inserted through the endoscope insertion passage 306 of the outer tube 300 and the endoscope insertion part 102 is mounted on the outer tube 300 by engagement with the slider body 402 will be described.

Figure 15:
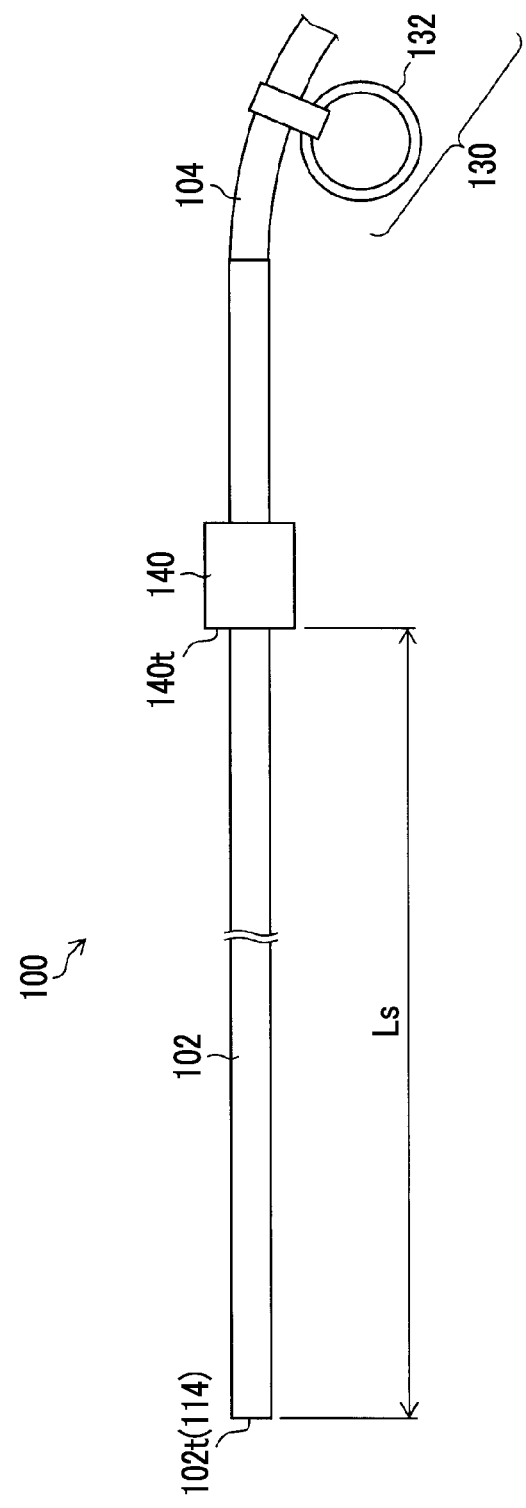
FIG. 15 is a side view of an endoscope including a positioning part.
Figure 16:
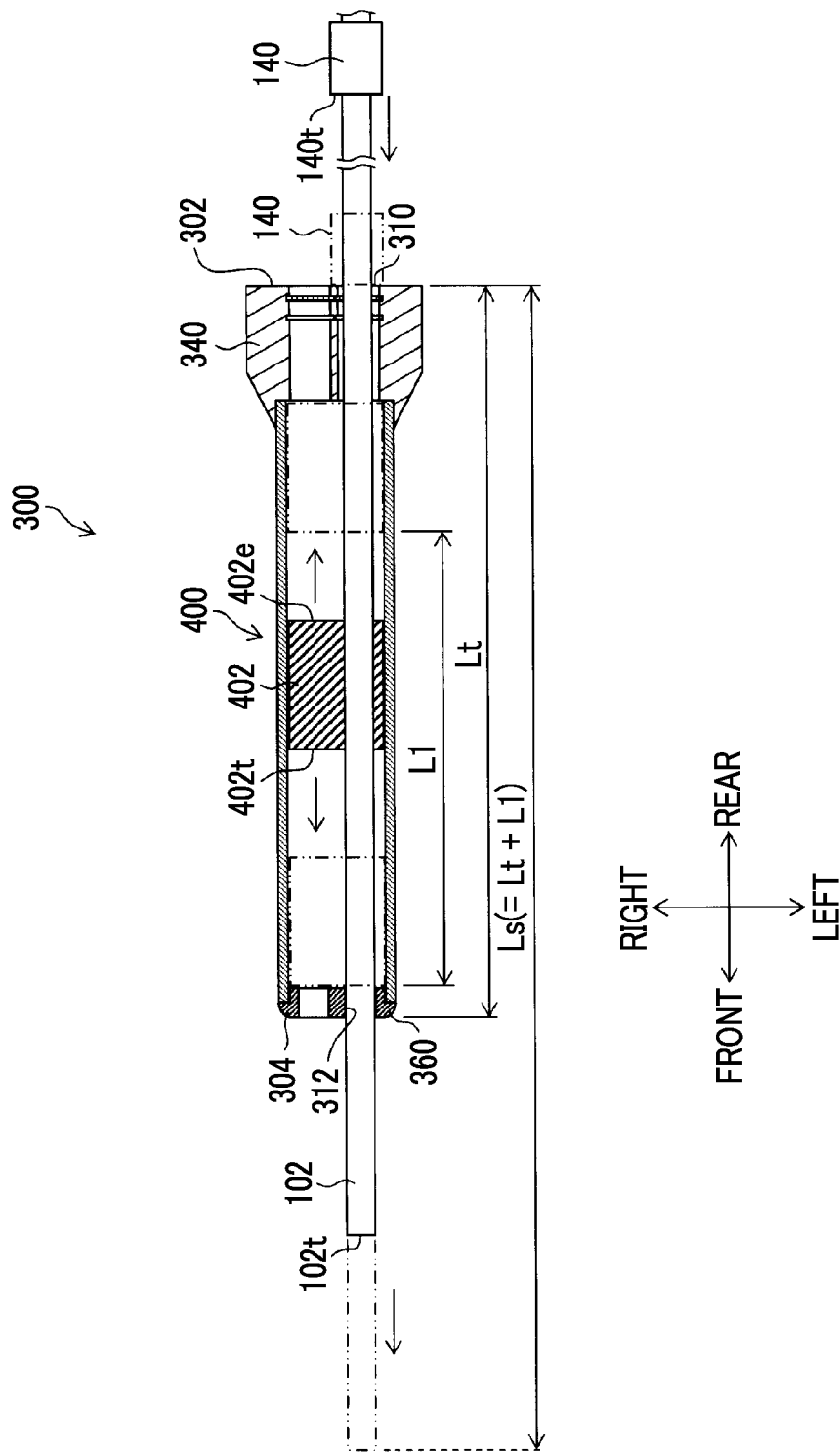
FIG. 16 is a schematic cross sectional view of the outer tube through which the endoscope including the positioning part is inserted.

FIG. 15 is a side view illustrating the endoscope 100 including a positioning part that constitutes a positioning means, and FIG. 16 is a schematic cross sectional view of the outer tube 300 through which the endoscope 100 is inserted. In addition, in FIG. 16 and FIGS. 17 to 20 illustrated hereinbelow, only the slider body 402 of the slider 400 is illustrated in a simplified manner as a quadrangular block.

As illustrated in these drawings, the larger-diameter part 140 is provided on the base end side of the endoscope insertion part 102 of the endoscope 100, as the positioning part that constitutes the positioning means. The endoscope insertion part 102 has a substantially constant diameter in portions other than the larger-diameter part 140, and the larger-diameter part 140 forms a shaft part that has a larger external diameter than the diameter of the portions other than larger-diameter part 140.

Additionally, the larger-diameter part 140 is formed, for example, in a columnar shape, and the external diameter thereof is larger than the diameter (internal diameter) of the first base end opening 310 in the base end surface 302 of the outer tube 300. The larger-diameter part 140 constitutes an abutment part that is not insertable through the endoscope insertion passage 306 of the outer tube 300.

Hence, if the endoscope insertion part 102 is inserted from the first base end opening 310 of the outer tube 300 and is moved forward as illustrated in FIG. 16, a distal end 140t of the larger-diameter part 140 abuts against the base end surface 302 of the outer tube 300 from the base end side. Accordingly, the position of the endoscope insertion part 102 capable of being inserted into the endoscope insertion passage 306 of the outer tube 300 is limited to a range up to a position where the distal end 140t of the larger-diameter part 140 abuts against the base end surface 302 of the outer tube 300.

That is, the maximum insertion length of the outer tube 300 such that the endoscope insertion part 102 can be inserted into the endoscope insertion passage 306 of the outer tube 300 becomes a length Ls from a distal end 102t (distal end surface 114) of the endoscope insertion part 102 to the distal end 140t of the larger-diameter part 140.

Meanwhile, as illustrated in FIG. 16, if the length (hereinafter simply referred to the length of the outer tube 300) in a direction of a reference axis 300a from the distal end surface 304 of the outer tube 300 to the base end surface 302 is defined as Lt and the length of the movable range of the slider 400 (slider body 402) is defined as L1, the distal end 140t of the larger-diameter part 140 is provided at a position apart by Lt+L1 from the distal end 102t of the endoscope insertion part 102 toward the base end side, and the length Ls coincides with Lt+L1.

Here, the movable range of the slider 400 (slider body 402) means a movement range from a first position (equivalent to the front end of the above-described movable range) where the movement of the slider 400 (slider body 402) to the distal end side is restricted by a first stopper on the distal end side to a second position (equivalent to a rear end of the above-described movable range) where the movement of the slider 400 (slider body 402) to the base end side is restricted by a second stopper on the base end side. In FIG. 16, with the position of the distal end 402t of the slider body 402 as a reference, a range from the position of the distal end 402t of the slider body 402 when the slider body 402 reaches the first position with respect to the long tubular outer tube body 320 to the position of the distal end 402t of the slider body 402 when the slider body reaches the second position is illustrated as the movable range of the slider 400.

Additionally, the length L1 of the movable range of the slider 400 is equivalent to the movement distance of the slider 400 (slider body 402) when the slider 400 moves from the first position to the second position.

Moreover, in the present embodiment, the position of the slider 400 when the distal end 402t of the slider body 402 abuts against the distal end cap 360 is the first position, and the distal end cap 360 is equivalent to the above-described first stopper. Additionally, the position of the slider 400 when a base end 402e of the slider body 402 abuts against the base end cap 340 is the second position, and the base end cap 340 is equivalent to the above-described second stopper. However, since the movable range of the slider 400 can be restricted by arbitrary restriction means, the first stopper and the second stopper can be different from those of the present embodiment.

According to the larger-diameter part 140 provided in the endoscope insertion part 102 as the positioning part as described above, if the endoscope insertion part 102 is moved forward when the endoscope insertion part 102 is mounted on the outer tube 300, that is, when the endoscope insertion part 102 is inserted from the first base end opening 310 of the outer tube 300 and is coupled to the slider body 402, the distal end 102t of the endoscope insertion part 102 abuts against or engages with the pressure-contact member 426 in the endoscope-coupling part 420 of the slider body 402.

Figure 17:
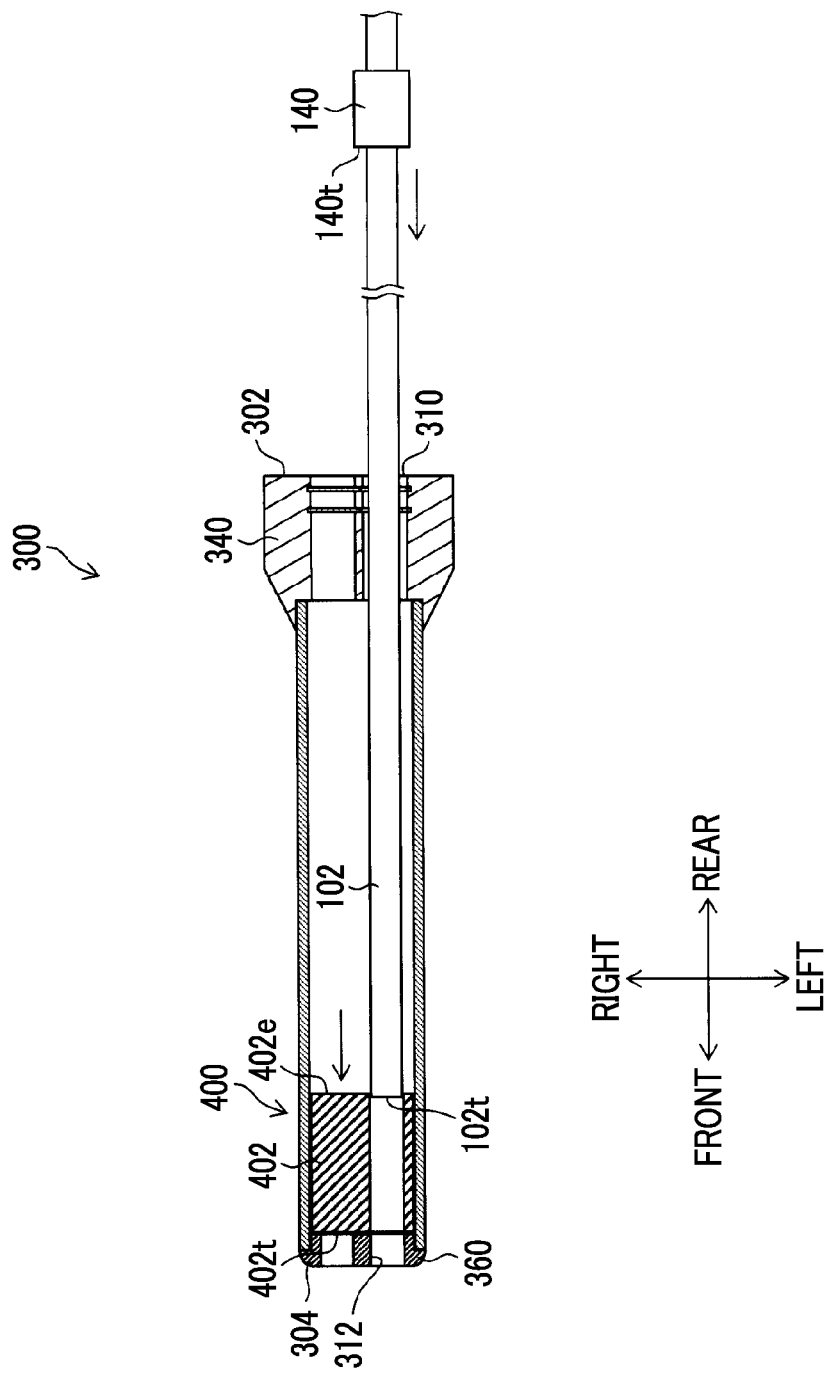
FIG. 17 is a view illustrating a state when a slider body of the outer tube is mounted on the endoscope insertion part at a predetermined position.

Subsequently, if the endoscope insertion part 102 is moved forward, the slider body 402 is moved forward together with the endoscope insertion part 102, and as illustrated in FIG. 17, the distal end 402t of the slider body 402 abuts against the distal end cap 360 (the first stopper), and the slider body 402 reaches the first position that is the front end of the movable range.

Figure 18:
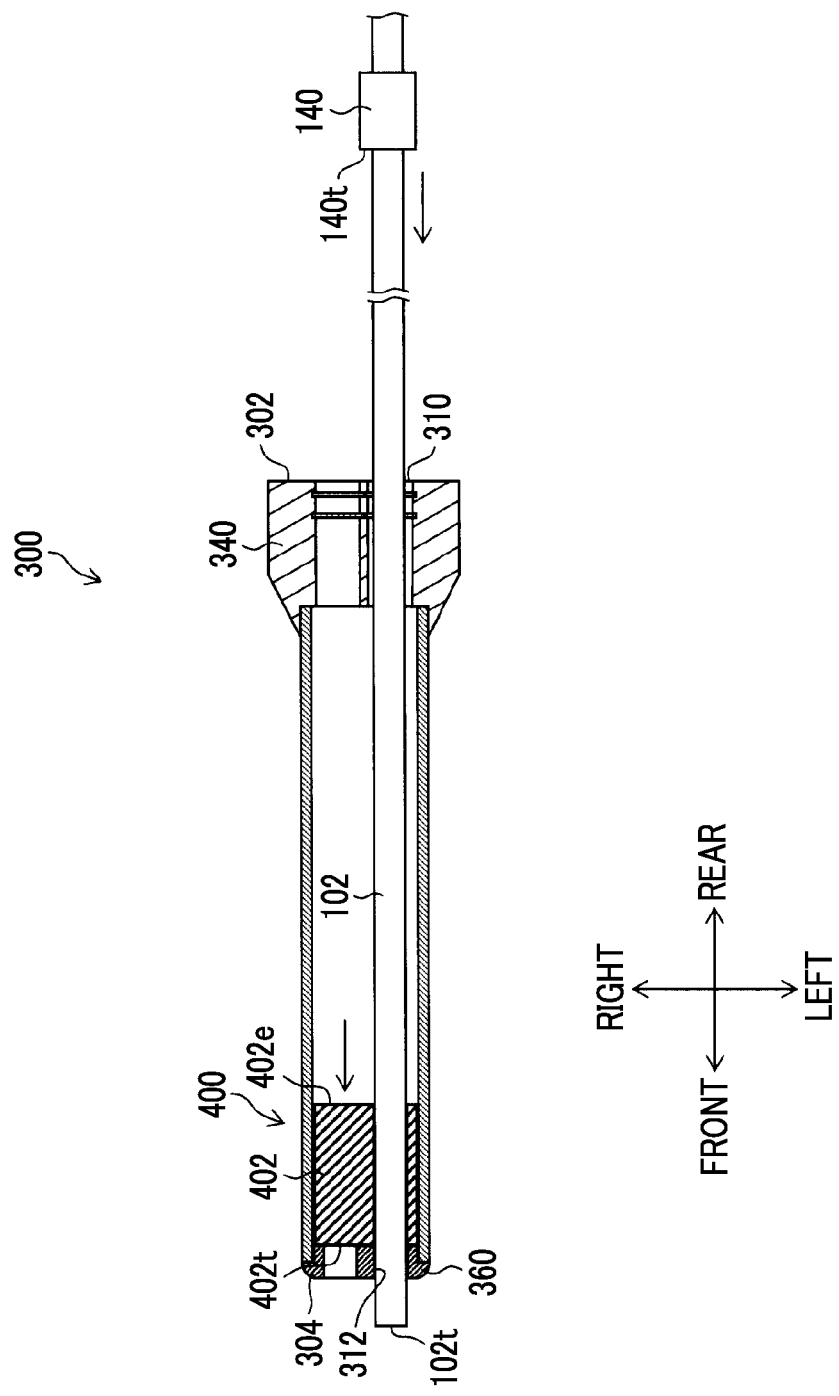
FIG. 18 is a view illustrating a state when the slider body of the outer tube is mounted on the endoscope insertion part at a predetermined position.

Moreover, if the endoscope insertion part 102 is moved forward, the endoscope insertion part 102 is moved forward with respect to the pressure-contact member 426 while the endoscope insertion part 102 comes into sliding contact with the pressure-contact member 426 of the slider body 402. Then, as illustrated in FIG. 18, the endoscope insertion part 102 is delivered from the first distal end opening 312 of the distal end surface 304 of the outer tube 300, and the delivery length (amount of protrusion) of the endoscope insertion part 102 from the distal end surface 304 increases.

Figure 19:
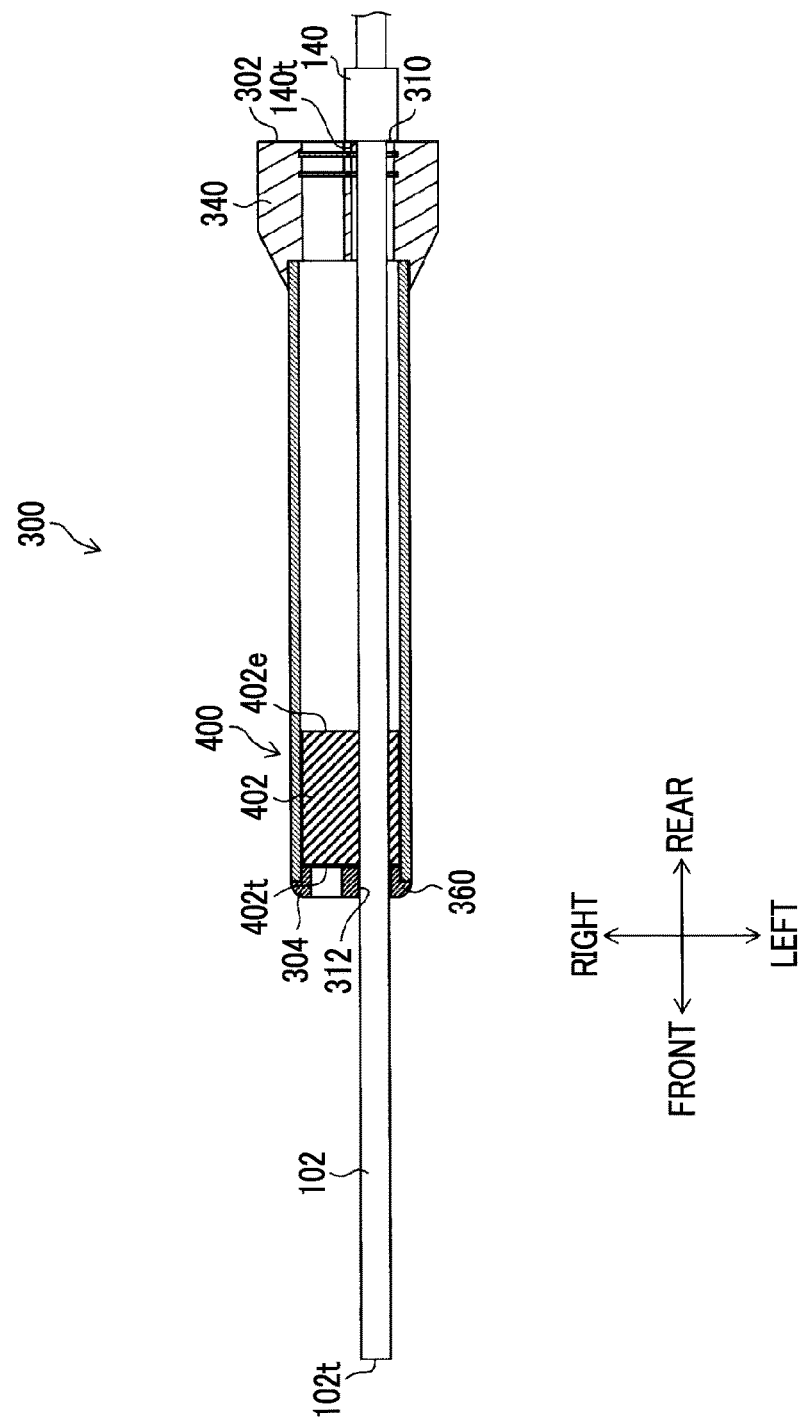
FIG. 19 is a view illustrating a state when the slider body of the outer tube is mounted on the endoscope insertion part at a predetermined position.

Then, if the endoscope insertion part 102 is further moved forward, finally, as illustrated in FIG. 19, the distal end 140t of the larger-diameter part 140 of the endoscope insertion part 102 moves to a position where this distal end abuts against the base end surface 302 of the outer tube 300, and the forward movement thereof is restricted.

In this way, when the endoscope insertion part 102 is mounted on the outer tube 300, the operator that uses the endoscope 100 and the outer tube 300 of the present embodiment is made to know that the distal end 140t of the larger-diameter part 140 that the endoscope insertion part 102 is inserted to a predetermined position where this distal end abuts against the base end surface 302 of the outer tube 300 well in advance.

Accordingly, when the endoscope insertion part 102 is mounted on the outer tube 300, the endoscope insertion part 102 is inserted through the endoscope insertion passage 306 of the outer tube 300 and the position of the distal end 140t of the larger-diameter part 140 is matched with the position of the base end of the outer tube 300, that is, the larger-diameter part 140 is made to abut against the base end surface 302 of the outer tube 300. Thus, irrespective of the operator and irrespective of every use (mounting), the endoscope insertion part 102 can be easily positioned at a predetermined position with respect to the outer tube 300, and the slider body 402 can be coupled to (engaged with) the endoscope insertion part 102 at the predetermined position.

Figure 20:
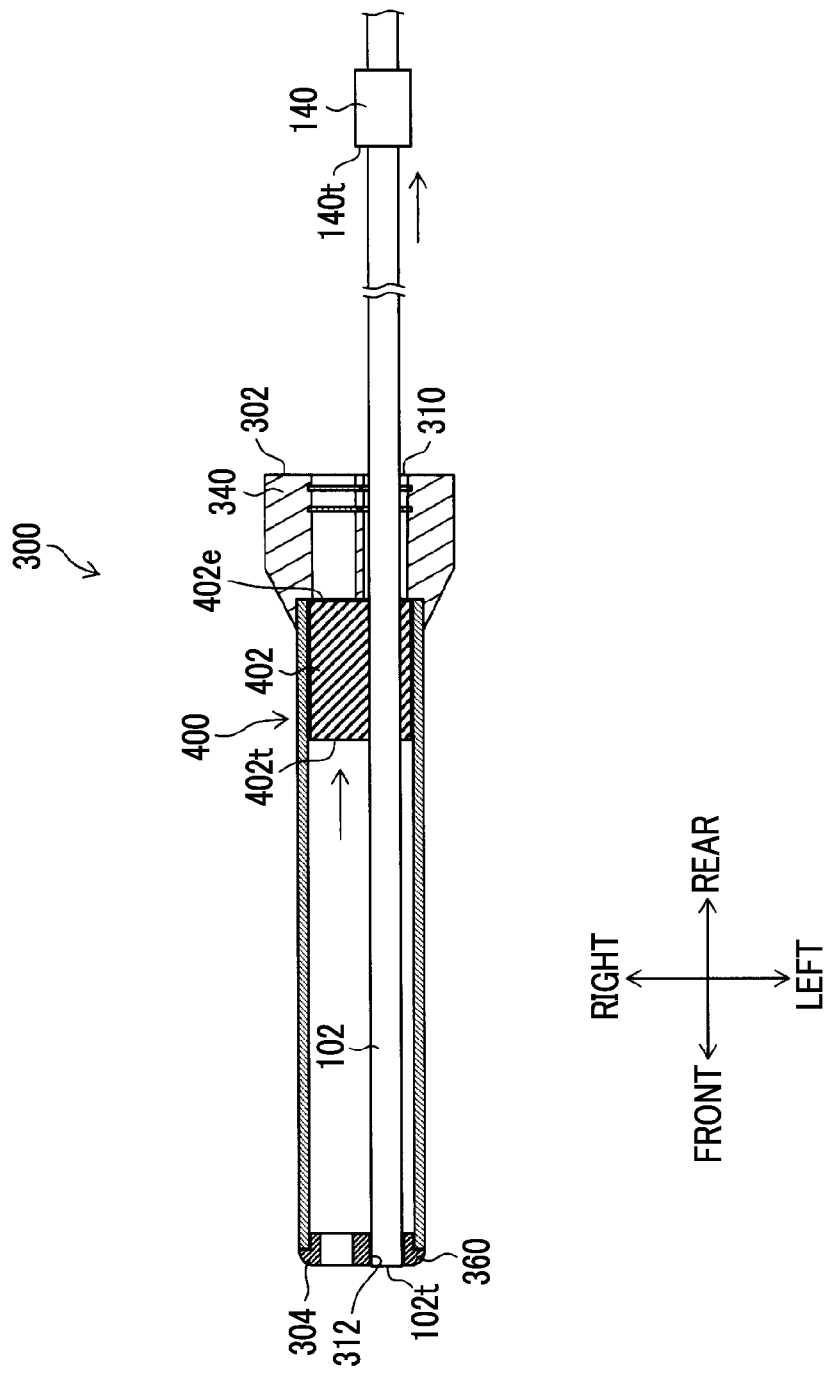
FIG. 20 is a view illustrating a state where the endoscope insertion part is moved backward nearest to a base end side after the slider body of the outer tube is mounted on the endoscope insertion part at a predetermined position.

Then, when the distal end 140t of the larger-diameter part 140 of the endoscope insertion part 102 moves the endoscope insertion part 102 backward from the position where this distal end front abuts against the base end surface 302 of the outer tube 300, and as illustrated in FIG. 20, the base end 402e of the slider body 402 abuts against the base end cap 340 (second stopper) and the slider body 402 reaches the second position that is the rear end of the movable range, the distal end 102t of the endoscope insertion part 102 is disposed at a position where this distal end substantially coincide with the distal end surface 304 of the outer tube 300.

Hence, when the operator operates to move the endoscope 100, or the treatment tool 200 inserted through the treatment tool insertion passage 308 forward and backward, to move the endoscope insertion part 102 forward and backward in the operation of the operator at the time of the treatment after the mounting of the endoscope insertion part 102 onto the outer tube 300, the observation window 116 provided in the distal end surface 114 of the endoscope insertion part 102 does not enter the inside of the outer tube 300 even in a case where the slider 400 (slider body 402) reaches the second position that is the rear end of the movable range. Accordingly, a situation where the range of the observation visual field of the observation part of the endoscope 100 that picks up an image of a part to be observed using the solid state image pickup element via the observation window 116 is blocked by the outer tube 300 and becomes narrow is prevented in advance. Also, the endoscope 100 can be appropriately and easily mounted on the outer tube 300, without causing the time and effort for resume mounting work of the endoscope 100 onto the outer tube 300.

Additionally, since it is possible to recognize, during treatment, that the slider body 402 reaches the first position that is the front end of the movable range from the larger-diameter part 140 of the endoscope insertion part 102 being located at the base end of the outer tube 300 or abutting against the base end (base end surface 302) of the outer tube 300, excellent situation recognition can be made. Treatment performance is improved by virtue of the excellent situation recognition.

As described above, in the endoscope 100, it is possible to adopt a form in which the distal end 140t of the larger-diameter part 140 is provided at the position apart by at least Lt+L1, that is, the position apart by Lt+L1 or more from distal end 102t of the endoscope insertion part 102 to the base end side. Even in such a case, the same effects as the above-described effects are obtained.

Figure 21:
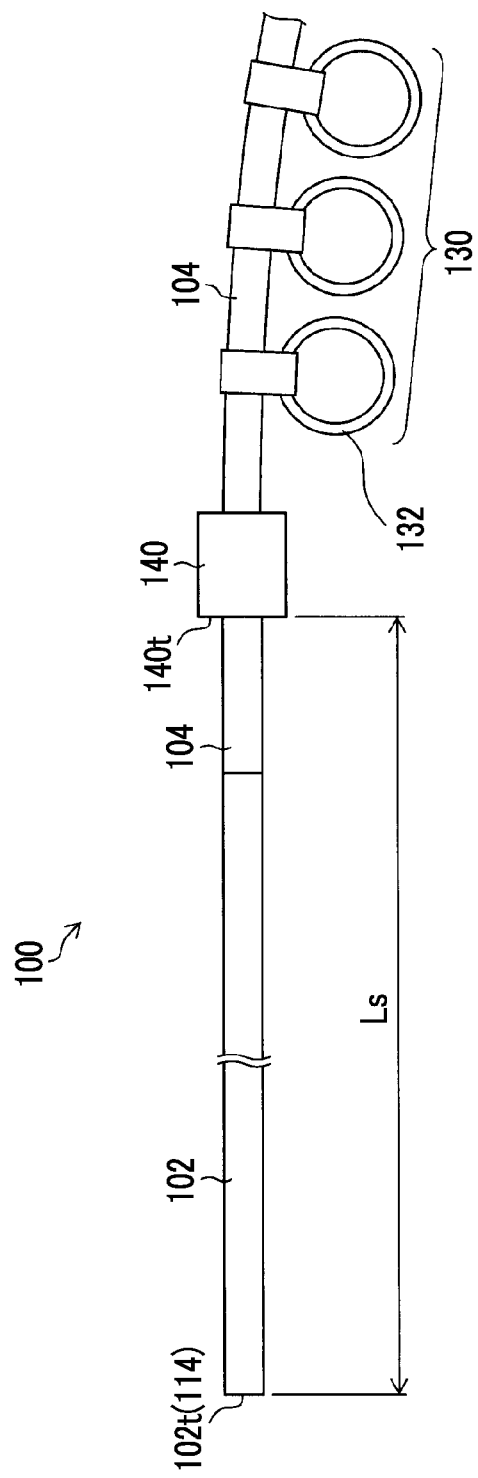
FIG. 21 is a side view illustrating the endoscope including the positioning part and illustrating the endoscope including the positioning part in a cable part.

Additionally, a case where the position where the larger-diameter part 140 apart by Lt+L1 or more from the distal end 102t of the endoscope insertion part 102 to the base end side is provided falls within the range of the cable part 104 may occur depending on the length of the endoscope insertion part 102, the length of the outer tube 300, and the length of the movable range of the slider body 402. In such a case, as illustrated in FIG. 21, the larger-diameter part 140 can also be provided in the cable part 104. However, it is desirable that the larger-diameter part 140 is provided nearer to the distal end side than the base end of the endoscope insertion part 102, that is provided within a range of the endoscope insertion part 102.

Moreover, the larger-diameter part 140 can be made to serve also as the operating part by gripped an operational personnel, such as the operator, when performing operation, such as the forward and backward movement operation, rotational operation, or the like of the endoscope 100. In a case where the position where the larger-diameter part 140 is provided overlaps a position where the forward and backward movement operating part 130 is provided, or in a case where the position where the larger-diameter part 140 is provided overlap the position where the forward and backward movement operating part 130 is provided intentionally, it is also possible to provide the larger-diameter part 140 as the forward and backward movement operating part 130 instead of the hooking part 132 of the forward and backward movement operating part 130.

In a case where the larger-diameter part 140 is made to serve also as the operating part in this way, especially, in a case where the larger-diameter part 140 serves also as the forward and backward movement operating part 130, the larger-diameter part 140 facilitates that the operator makes the index finger of his/her right hand having gripped the operating part 204 of the treatment tool 200 abut against an outer peripheral surface of the larger-diameter part 140 to perform the forward and backward movement operation of the endoscope 100. Therefore, it is desirable that the outer peripheral surface of the larger-diameter part 140 has shapes or materials that are difficult to slide. For example, it is desirable that at least one of an antislip shape or an antislip member is formed on the outer peripheral surface of the larger-diameter part 140.

Figure 22:
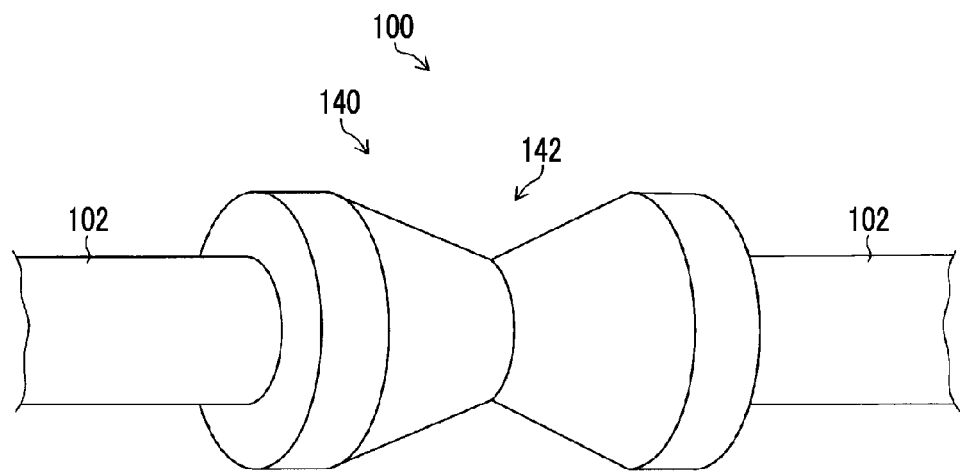
FIG. 22 is a view illustrating a form in a case where the positioning part of the endoscope is made to serve also as a forward and backward movement operating part.

For example, as the antislip shape, a neck part 142 (diameter-reduced part) that enables a finger to be hooked thereon may be formed on the outer peripheral surface of the larger-diameter part 140 as illustrated in FIG. 22.

Additionally, as the antislip shape, a shape in which irregularities are provided in the circumferential direction on the outer peripheral surface of the larger-diameter part 140 is considered. Here, the irregularities mean a state where a protrusion that protrudes from a reference plane with a side surface of the column as the reference plane and a recess that is depressed from the reference plane can be specified, when a column with a predetermined radius centered on an axis of the larger-diameter part 140 is assumed. Not only a shape such as a gear shape but also shapes, such as an elliptical shape and an oval shape, are included in the antislip shape.

Additionally, as the antislip member, a member that is made of materials with a larger frictional coefficient than the outer peripheral surface of the endoscope insertion part 102 or a member with surface properties with a larger frictional coefficient than the outer peripheral surface of the endoscope insertion part 102 can be considered. For example, a member in which resin, such as silicone rubber, is provided on the outer peripheral surface of the larger-diameter part 140, a member in which fine irregularities are provided on the outer peripheral surface of the larger-diameter part 140 through sandblast working or the like, or the like is considered.

In addition, the forward and backward movement operating part 130 is not necessarily provided in the cable part 104, and may also be provided in the endoscope insertion part 102. For example, even in a case where the larger-diameter part 140 is made to serve also as the forward and backward movement operating part 130, an aspect in which the larger-diameter part 140 is provided in the endoscope insertion part 102 is also considered.

Additionally, the positioning part provided in the above-described endoscope 100 may be not the abutment part that protrudes in a columnar shape like the larger-diameter part 140 but may be a projection part that protrudes so as not to be insertable through the endoscope insertion passage 306 of the outer tube 300. That is, any kind of shape may be adopted as long as the projection part that abuts against the base end surface 302 of the outer tube 300 is provided.

Figure 23:
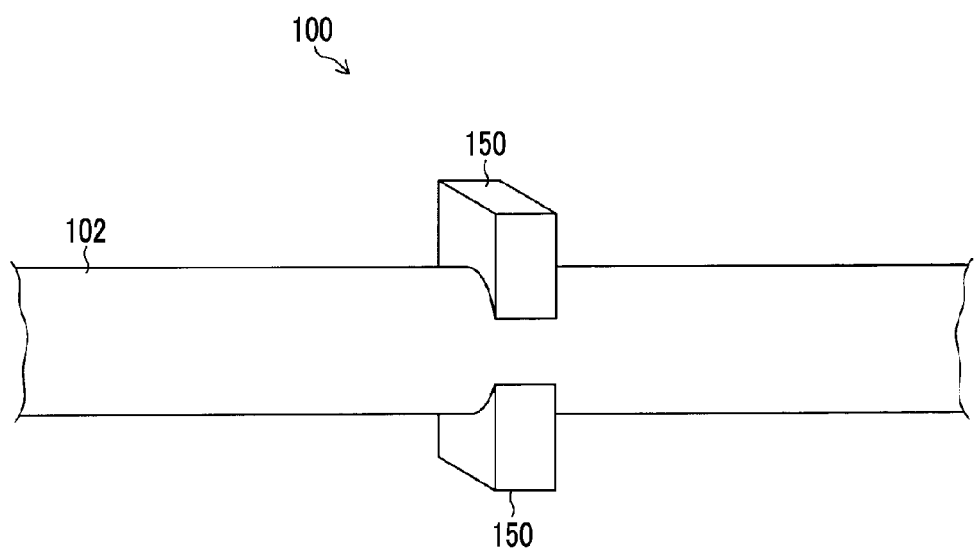
FIG. 23 is a view illustrating another form of the positioning part of the endoscope.

For example, as illustrated in FIG. 23, projection parts 150 that protrude radially outward may be provided in two places along the circumferential direction as illustrated in this drawing on the outer peripheral surface of the endoscope insertion part 102 (or the cable part 104). The projection part 150 may be provided in one place, and projection parts may be provided in three or more places in the circumferential direction. Additionally, the shape of the projection part 150 is not limited to specific one.

Moreover, the above-described larger-diameter part 140 or the above-described projection part 150 also act as an index indicating a position where the endoscope insertion part 102 (or cable part 104) is matched with the base end of the outer tube 300. The positioning part does not necessarily have a shape that protrudes so as not to be insertable through the endoscope insertion passage 306 of the outer tube 300, and may have a function as the index indicating the position where the endoscope insertion part 102 (or the cable part 104) is matched with the base end of the outer tube 300.

Figure 24:
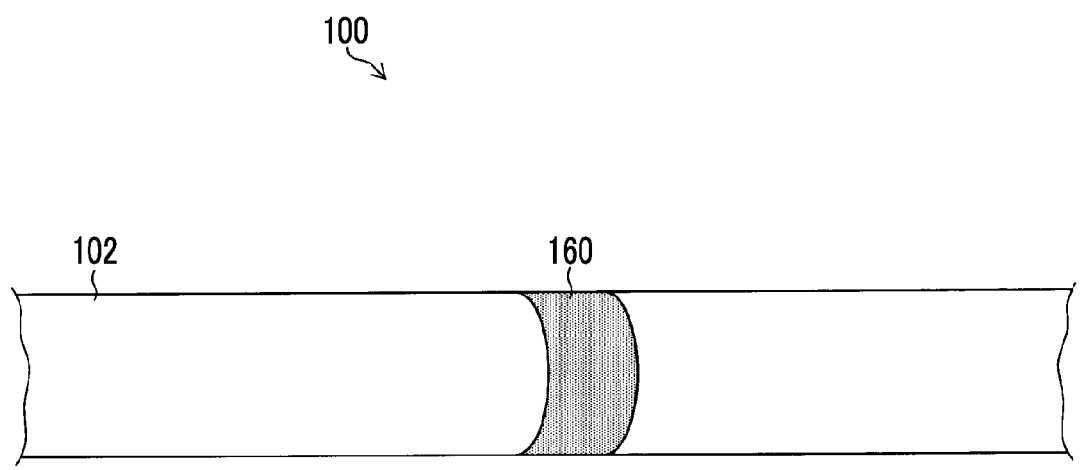
FIG. 24 is a view illustrating still another form of the positioning part of the endoscope.

For example, as illustrated in FIG. 24, the positioning part may be a marker 160 that is formed on the outer peripheral surface (surface) of the endoscope insertion part 102 (or the cable part 104). The marker 160 may be a monochromatic line or a monochromatic surface that is insertable through the endoscope insertion passage 306 and is different from other portions of the endoscope insertion part 102 (or the cable part 104) or may be one having a pattern.

In the above embodiment, a case where the invention is applied to the surgical apparatus for an endoscope 10 in which the slider 400 that is the interlocking member of the outer tube 300 has the sensing region and the non-sensing region has been described above. However, the invention can also be applied to a surgical apparatus for an endoscope in which the interlocking member of the outer tube 300 does not have the non-sensing region but has only the sensing region. Additionally, the specific configuration of the outer tube 300 illustrated in the above embodiment is an example, and is not limited to a specific configuration.

EXPLANATION OF REFERENCES

10: surgical apparatus for endoscope
100: endoscope
102: endoscope insertion part
104: cable part
108: processor device
110: light source device
112: monitor
114, 304: distal end surface
116: observation window
118: illumination window
130: forward and backward movement operating part
132: hooking part
140: larger-diameter part
142: neck part
150: projection part
160: marker
200: treatment tool
202: treatment tool insertion part
204: operating part
206: treatment part
210: fixed handle
214: movable handle
300: outer tube
300a: reference axis
302: base end surface
306: endoscope insertion passage
306a: endoscope insertion axis
308: treatment tool insertion passage
308a: treatment tool insertion axis
310: first base end opening
312: first distal end opening
314: second base end opening
316: second distal end opening
320: long tubular outer tube body
340: base end cap
346, 348: valve member
360: distal end cap
400: slider
402: slider body
420: endoscope-coupling part
422: treatment tool-coupling part
426, 446: pressure-contact member
440: sleeve
444: sleeve body
500: exterior tube
504: longitudinal groove
520: lateral groove

What is claimed is:
1. An endoscopic surgical apparatus comprising:
an endoscope having an observation window at a distal end thereof;
a treatment tool having a treatment part at a distal end thereof; and
an outer tube that passes through a body wall, is inserted into a body cavity, and guides the endoscope and the treatment tool into the body cavity,
wherein the outer tube includes
an outer tube body having a distal end, a base end, and a longitudinal axis,
a first distal end opening and a second distal end opening provided at the distal end of the outer tube body,
a first base end opening and a second base end opening provided at the base end of the outer tube body,
an endoscope insertion passage that is provided along the longitudinal axis of the outer tube body, allows the first distal end opening and the first base end opening to communicate with each other therethrough, and allows the endoscope to be inserted therethrough so as to be movable forward and backward,
a treatment tool insertion passage that is provided along the longitudinal axis of the outer tube body, allows the second distal end opening and the second base end opening to communicate with each other therethrough, and allows the treatment tool to be inserted therethrough so as to be movable forward and backward,
a slider that has an endoscope-coupling part coupled to the endoscope inserted through the endoscope insertion passage, and a treatment tool-coupling part coupled to the treatment tool inserted through the treatment tool insertion passage and is movable forward and backward inside the outer tube body, wherein the endoscope-coupling part comprises a through-hole, and the treatment tool-coupling part comprises a sleeve,
a distal end cap that is provided inside the outer tube body and restricts movement of the slider to the distal end side of the outer tube body, and
a base end cap that is provided inside the outer tube body and restricts movement of the slider to the base end side of the outer tube body, and
wherein the endoscope has a positioning part at a position apart by at least Lt+L1 from a distal end of the endoscope toward a base end side thereof when a movement distance of the slider is defined as L1 and a length of the outer tube body in a longitudinal axis direction is defined as Lt,
wherein the movement distance of the slider is from a first position where movement of the slider to the distal end side of the outer tube body is restricted by the distal end cap to a second position where movement of the slider to the base end side of the outer tube body is restricted by the base end cap.

2. The endoscopic surgical apparatus according to claim 1,
wherein the positioning part has a distal end that abuts against a base end surface of the outer tube body from the base end side.

3. The endoscopic surgical apparatus according to claim 2,
wherein the positioning part is gripped by an operator who operates the endoscope.

4. The endoscopic surgical apparatus according to claim 3,
wherein the positioning part has a shaft part having a larger external diameter than an internal diameter of the first base end opening.

5. The endoscopic surgical apparatus according to claim 4,
wherein the shaft part has an outer peripheral surface in which at least one of an antislip shape or an antislip member is formed.

6. The endoscopic surgical apparatus according to claim 1,
wherein the positioning part is a marker that is formed on a surface of the endoscope and indicates a position apart by at least Lt+L1 from the distal end of the endoscope toward the base end side thereof.

7. The endoscopic surgical apparatus according to claim 1,
wherein the positioning part is provided at a position apart by Lt+L1 from the distal end of the endoscope toward the base end side thereof.

8. The endoscopic surgical apparatus according to claim 1,
wherein the slider has a non-interlocking region where the forward and backward movement of either the endoscope or the treatment tool does not interlock with the movement of the other and a interlocking region where the forward and backward movement of either the endoscope or the treatment tool interlocks with the movement of the other.

* * * * *